US008455255B2

(12) United States Patent
Nakamura

(10) Patent No.: US 8,455,255 B2
(45) Date of Patent: Jun. 4, 2013

(54) METHOD FOR PRODUCTION OF NOVEL NANO SILICA PARTICLE AND USE OF THE NANO SILICA PARTICLE

(75) Inventor: Michihiro Nakamura, Tokushima (JP)

(73) Assignee: The University of Tokushima, Tokushima-shi, Tokushima (JP)

(*) Notice: Subject to any disclaimer, the term of this patent is extended or adjusted under 35 U.S.C. 154(b) by 375 days.

(21) Appl. No.: 12/303,870

(22) PCT Filed: Jun. 7, 2007

(86) PCT No.: PCT/JP2007/061587
§ 371 (c)(1),
(2), (4) Date: Sep. 8, 2010

(87) PCT Pub. No.: WO2007/142316
PCT Pub. Date: Dec. 13, 2007

(65) Prior Publication Data
US 2010/0330582 A1 Dec. 30, 2010

(30) Foreign Application Priority Data
Jun. 8, 2006 (JP) ................................ 2006-160107

(51) Int. Cl.
*G01N 33/552* (2006.01)
(52) U.S. Cl.
USPC ............... 436/19; 436/10; 436/524; 436/527
(58) Field of Classification Search
USPC ..................... 436/10, 19, 524, 527
See application file for complete search history.

(56) References Cited

U.S. PATENT DOCUMENTS

| | | | | |
|---|---|---|---|---|
| 3,642,445 A * | 2/1972 | Muter et al. | ............ | 423/244.08 |
| 4,246,209 A * | 1/1981 | Smith-Johannsen | ........... | 264/28 |
| 4,428,895 A * | 1/1984 | Blasch et al. | ................... | 264/28 |
| 4,683,334 A * | 7/1987 | Bergna et al. | ................... | 564/474 |
| 4,775,520 A * | 10/1988 | Unger et al. | ................... | 423/335 |
| 4,927,749 A * | 5/1990 | Dorn | ............................... | 435/2 |
| 5,362,473 A * | 11/1994 | Panek | .......................... | 424/1.13 |
| 5,414,114 A * | 5/1995 | Palacios | ........................ | 562/556 |
| 5,939,182 A * | 8/1999 | Huang et al. | ................. | 428/323 |
| 6,004,899 A * | 12/1999 | Tachizawa | .................... | 503/207 |

(Continued)

FOREIGN PATENT DOCUMENTS

| | | |
|---|---|---|
| JP | 03-047840 | 2/1991 |
| JP | 03-269020 | 11/1991 |

(Continued)

OTHER PUBLICATIONS

Hernandez, G. et al, Journal of Non-Crystalline Solids 1999, 246, 209-215.*

(Continued)

*Primary Examiner* — Arlen Soderquist
(74) *Attorney, Agent, or Firm* — Seed IP Law Group PLLC

(57) ABSTRACT

The present invention presents a silica particle containing at least one silica compound selected from a group consisting of mercapto-propyl-trimethoxysilane (MPS), mercapto-propyl-triethoxysilane (MPES), mercapto-propyl-methyldimethoxysilane (MPDMS), trimethoxy[2-(7-oxabicyclo[4.1.0]-hepto-3-yl)ethyl]silane (EpoPS), thiocyanatopropyltriethoxysilane (TCPS), and acryloxypropyltrimethoxysilane (AcPS), which can be provided and utilized as a label, a marker, or the like for qualitative test and quantitative test for such as prophylactic agent, therapeutic agent, diagnostic agent, diagnostic and therapeutic agent or the like in dental, medical and veterinary fields regardless of fields.

26 Claims, 27 Drawing Sheets

U.S. PATENT DOCUMENTS

| | | | |
|---|---|---|---|
| 6,160,067 A * | 12/2000 | Eriyama et al. | 526/279 |
| 6,416,838 B1 * | 7/2002 | Arney et al. | 428/64.7 |
| 6,417,246 B1 * | 7/2002 | Jia et al. | 523/113 |
| 6,548,168 B1 * | 4/2003 | Mulvaney et al. | 428/402 |
| 6,719,535 B2 * | 4/2004 | Rakestraw et al. | 417/50 |
| 6,787,629 B2 * | 9/2004 | Jia et al. | 528/196 |
| 6,921,576 B2 * | 7/2005 | Terauchi et al. | 428/404 |
| 7,033,975 B2 * | 4/2006 | Baran et al. | 507/102 |
| 7,196,340 B2 * | 3/2007 | Hagiwara et al. | 250/484.4 |
| 7,919,333 B2 * | 4/2011 | Muller-Schulte | 436/526 |
| 7,947,461 B2 * | 5/2011 | Aizawa et al. | 435/7.1 |
| 2003/0124564 A1 | 7/2003 | Trau et al. | 435/6 |
| 2003/0148544 A1 * | 8/2003 | Nie et al. | 436/524 |
| 2004/0076681 A1 * | 4/2004 | Dennis et al. | 424/489 |
| 2006/0018966 A1 * | 1/2006 | Lin et al. | 424/484 |
| 2006/0110733 A1 * | 5/2006 | Toohey et al. | 435/6 |
| 2008/0241044 A1 * | 10/2008 | Kuebelbeck | 423/335 |
| 2008/0293584 A1 * | 11/2008 | Aizawa et al. | 506/9 |
| 2010/0310872 A1 * | 12/2010 | Nakamura | 428/405 |
| 2010/0330582 A1 * | 12/2010 | Nakamura | 435/7.1 |

FOREIGN PATENT DOCUMENTS

| | | |
|---|---|---|
| JP | 04-114065 | 4/1992 |
| JP | 04-202325 | 7/1992 |
| JP | 2000-239388 | 9/2000 |
| JP | 2002-173612 | 6/2002 |
| WO | WO 03/002633 A1 | 1/2003 |
| WO | 2005/085135 A1 | 9/2005 |
| WO | WO 2006/070852 A1 | 7/2006 |
| WO | WO 2007/074722 A1 | 7/2007 |

OTHER PUBLICATIONS

Etienne, M. et al, Studies in Surface Science and Catalysis 2002, 141, 615-622.*

Ten Brinke, J. W. et al, Macromolecules 2002, 35, 10026-10037.*

Walcarius, A. et al, Chemistry of Materials 2003, 15, 4181-4192.*

Ganesan, V. et al, Langmuir 2004, 20, 3632-3640.*

Miller, C. R. et al, Langmuir 2005, 21, 9733-9740.*

Costa, C. A. R> et al, Journal of Physical Chemistry B 2003, 107, 4747-4755.*

Nakamura et al., "Synthesis and Characterization of Organosilica Nanoparticles Prepared from 3-Mercaptopropyltrimethoxysilane as the Single Silica Source," *J. Phys. Chem C* 111:18892-18898, 2007.

Tan et al., "Bionanotechnology Based on Silica Nanoparticles," *Medicinal Research Reviews* 24(5):621-638, 2004.

Taylor et al., "Mesoporous Silica Nanospheres as Highly Efficient MRI Contrast Agents," *J. Am. Chem. Soc.* 130:2154-2155, 2008.

* cited by examiner (a)

(b)

(a)

(b)

METHOD FOR PRODUCTION OF NOVEL NANO SILICA PARTICLE AND USE OF THE NANO SILICA PARTICLE

FIELD OF THE INVENTION

The present invention relates to a method for producing a novel nano silica particle and application thereof. More specifically, the present invention relates to an MPS particle (MPS: 3-mercapto-propyltrimethoxysilane, or 3-mercapto-propyltriethoxysilane; hereafter to be abbreviated as "MPS") that is a silica particle or a silica sphere that has remarkably excellent features as compared with conventional silica particles. Further, in the present specification, preparation of silica particles having remarkably excellent features by various silica supply sources in addition to MPS will be described.

BACKGROUND ART

Technologies relating to production method and application of a silica particle or a silica sphere have been studied and developed throughout the world in great variety of ways, and a part of these technologies are put into practical use in improvement of incandescent lamp, bioassay, or the like. For synthesis thereof, usual practice is used or TEOS (tetraethylorthosilane; hereafter to be abbreviated as "TEOS") is normally used as the starting material, and conventional silica particles are TEOS particles. However, since surface layer of such TEOS particles has lower chemical reactivity (binding ability to foreign protein or nucleic acid), activation by introduction of acceptor group based on a silica compound other than the TEOS has been attempted (Patent Document 1). For example, as silica compound, tetraethoxysilane (OH group), mercapto-propylethoxysilane (SH group), amino-propylethoxysilane ($NH_2$ group) (one in parenthesis is "acceptor group" to be introduced) and the like are known. In other words, conventional activated silica particles have double structure composed of inner shell comprising TEOS and outer shell comprising acceptor group, and costs of time, labor, and the like required for producing thereof have been expensive. As described above, conventionally, preparation of silica particle has been generally made using tetraethoxysilane (TEOS) and the number of reports dealing with preparation of particles from other silica compounds such as MPS is small. The reason for this is considered that while the number of binding sites (Si—O) for silica network formation is four in TEOS, preparation of the particle by selecting other silica compounds with binding site inevitably three or less is not easy task. In fact, even if preparation of particles is attempted by MPS under particle preparation conditions using ordinary TEOS, particles are not prepared favorably. Further, among cases where MPS or the like is actually used, in the production of the MPS, the technology for obtaining MPS particle is known (Patent Document 2) in which MPS are pretreated (for 2-5 days at room temperature) with only hydrochloric acid (or mixed solution of hydrochloric acid and cetylmethylammonium chloride), ammonia water is added thereto and mixed, and are further reacted for 2 days at room temperature. However, this technology has such drawbacks that it lacks progressivity with regard to production costs as compared with conventional technology, production process is cumbersome and impractical, and the number of days required for producing particle is significant. In addition, adjustments of size (particle diameter) of particles thus prepared are difficult.

MPS particles obtained according to the method disclosed by Patent Document 2 is advantageous in that cavity formation characteristics is high and surface area is expanded due to cavities formed. However, in light of the fact that the technology as described in Patent Document 1 has been already developed, in which functional materials are bound to silica compound to be mixed with reaction solution for particle formation, and incorporated to particle lattice to allow functional materials to be contained in particle at high concentration, the amount of functional materials which may be contained in one particle becomes higher with lower cavity formation characteristics, and this is useful by just that much, and therefore, the method described in Patent Document 2 resulting in higher cavity formation characteristics can not be said to be useful for a case where the object is to take functional materials. As for the cavity formation characteristics, when cavity formation characteristics is high in the particle, internal structure is reduced and site where functional materials can be arranged is reduced, and this is disadvantageous for internal functionalization (fluorescence intensity per one particle is low). Further, when cavity formation characteristics is high, although surface area increases in some case, there are problems of control of void content and control of functional material arrangement (quantitative arrangement is difficult), and therefore, this can not be said to be useful unless effective embodiment is exemplified. Meanwhile, when cavity formation characteristics is low, internal structure increases, site where functional materials can be arranged increases, and this is advantageous for internal functionalization (fluorescence intensity per one particle is high). Further, with lower cavity formation characteristics, the surface area is simple surface area only, this surface area correlates with particle diameter, quantitative arrangement of functional materials becomes possible, and this is useful for quantitative analysis. Therefore, it can be said that one of superiorities which "non-pored" particle has to be utilized as size marker or fluorescent marker is high ability of internal functionalization.

In regard to adsorptive capacity characteristics of silica to DNA, protein or the like, with particles having many pores as described in Patent Document 2, effective adherence area to which DNA and protein adhere is not depending on surface area only based on diameter of particles, and adherence surface area varies according to size, number, position of pores, and it is therefore considered that parameters of adherence area are diversified, thereby causing a problem with quantitative characteristics. (It is considered that a difference is easily caused within a lot prepared and between lots prepared, and no finding is shown in Patent Document 2 that quantification was actually possible.) Therefore, if non-pored silica particles are realized, effective adherence area simply depends on particle diameter of the particle, surface area can then be determined by particle size, which is advantageous for quantitative experiments, and there are needs for preparation of such particles.

Patent Document 1: International publication WO No. 2006/070582 pamphlet
Patent Document 2: International publication WO No. 2003/002633 pamphlet

DISCLOSURE OF THE INVENTION

Problems to be Solved by the Invention

An object of the present invention is to resolve problems with prior art as described above. Specific example of problems include drawbacks of conventional type silica particles as described above including TEOS particles, such as high production costs, and low chemical reactivity (binding ability to foreign protein or nucleic acid). The object of the present invention is to provide silica particles in which functionality and quality are excellent and yet mass production is possible with low costs as compared with conventional silica particles.

Means for Solving the problems

SUMMARY OF THE INVENTION

The present invention has been completed by originality and ingenuity, and diligence efforts extended thus far based on a discovery of an extraordinary phenomenon that "MPS particles are produced quickly if ammonia water is added to MPS, which is conventionally used as ligand agent, mixed, and then heated".

Therefore, the followings are provided by the present invention:

(A1) A silica particle including at least one silica compound selected from a group consisting of mercapto-propyltrimethoxysilane (MPS), mercapto-propyltriethoxysilane (MPES), mercapto-propylmethyldimethoxysilane (MPDMS), trimethoxy[2-(7-oxabicyclo[4.1.0]-hepto-3-yl)ethyl] silane (EpoPS), thiocyanatopropyltriethoxysilane (TCPS), and acryloxypropyltrimethoxysilane (AcPS);

(A2) The silica particle according to Item A1, including a functional material in surface layer or therein, wherein the functional material is selected from a group consisting of fluorescent material, protein, nucleotide, oligonucleotide, sugar chain and combination thereof;

(A3) The silica particle according to Item A2, wherein when the functional material is a fluorescent material, the fluorescent material is selected from a group consisting of rhodamine red, fluorescein, hexanoic acid-6-(tetramethylrhodamine-5-carboxamide), hexanoic acid-5-(tetramethylrhodamine-5-carboxamide), Alexa Fluor 647, DY 635, DY 485, DY 495, DY 505 and trisdichlororuthenium (II) hexahydrate, and the fluorescent material is contained inside or exists on the surface layer independently or in the form of being bound to a compound selected from N-hydroxy succinimide (NHS), isothiocyanate (ITC) and maleimide;

(A4) A group of silica particles containing the silica particle according to any one of Items A1-3;

(A5) A standard marker including the silica particle according to any one of Items A1-3 or the group of silica particles according to Item A4, used for flow cytometry, size marker, beads assay and probe;

(A6) A support including the silica particle according to any one of Items A1-3 or the group of silica particles according to Item A4, used for synthesis of nucleic acid or protein, or cell culture application.

(A7) A preparation method of a silica particle or a group of silica particles comprising;

(a) a step for preparing a mixture of silica compound and ammonia water; and (b) a step for reacting the silica compound and the ammonia water under a predetermined temperature condition, wherein the silica compound is at least one silica compound selected from a group consisting of mercapto-propyl-trimethoxysilane (MPS), mercapto-propyl-triethoxysilane (MPES), mercapto-propyl-methyldimethoxysilane (MPDMS), trimethoxy[2-(7-oxabicyclo[4.1.0]-hepto-3-yl)ethyl]silane (EpoPS), thiocyanatopropyltriethoxysilane (TCPS), and acryloxypropyltrimethoxysilane (AcPS), and wherein, the method is performed so that ammonia water and temperature condition insteps (a) and (b) satisfy either of or both of the following conditions:

(i) high temperature (in a range of 80-100° C.); and
(ii) high ammonia concentration (final concentration not less than 250);

(A8) The method according to Item A7, wherein said step (b) is performed in the presence of isopropanol;

(A9) The method according to Item A7, wherein said temperature condition is room temperature, or concentration of ammonia water is not less than 20 and not more than 5% at final concentration;

(A10) A group of silica particles, (1) having average particle diameter adjusted in a range of 5 nm-5 μm that is a range of nano size to micron size, and
(2) having narrow area distribution with distribution width of particle diameter within ±250 of average particle diameter;

(A11) The group of silica particles according to Item A10, including the silica particles according to any one of Items A1-3; and (A12) The silica particle according to any one of Items A1-3, having at least one feature selected from a group consisting of:

(1) being non-pored;
(2) being free from macropore;
(3) being substantially in spherical shape;
(4) being free from pore not less than 20 nm;
(5) pore volume being not more than 0.1 ($m^3/g$); and
(6) particle diameter being in a range of 5 nm-5 μm.

The followings are also provided by the present invention:

(B1) A silica particle with non-pored surface layer;
(B2) A silica particle free from macropore;
(B3) A silica particle substantially in spherical shape;
(B4) The silica particle according to any one of Items B1-3, free from pore not less than 20 nm;
(B5) The silica particle according to any one of Items B1-4, having at least one feature selected from a group consisting of:

(1) being non-pored;
(2) being free from macropore;
(3) being substantially in spherical shape;
(4) being free from pore not less than 20 nm;
(5) pore volume being not more than 0.1 ($m^3/g$); and
(6) particle diameter being in a range of 5 nm-5 μm;

(B6) The silica particle according to any one of Items B1-5, wherein particle diameter is in a range of 5 nm-5 μm;

(B7) The silica particle according to any one of Items B1-6, produced from a silica compound selected from a group consisting of mercapto-propyl-trimethoxysilane (MPS), mercapto-propyl-triethoxysilane (MPES), mercapto-propyl-methyldimethoxysilane (MPDMS), trimethoxy[2-(7-oxabicyclo[4.1.0]-hepto-3-yl)ethyl]silane (EpoPS), thiocyanatopropyltriethoxysilane (TCPS), and acryloxypropyltrimethoxysilane (AcPS);

(B8) The silica particle according to any one of Items B1-7, having functional material;

(B9) The silica particle according to Item B8, having said functional material on surface layer of said silica particle;

(B10) The silica particle according to Item B8, having said functional material inside said silica particle;

(B11) The silica particle according to any one of Items B8-10, wherein said functional material is selected from a group consisting of fluorescent material, protein, nucleotide, oligonucleotide, sugar chain and combination thereof;

(B12) The silica particle according to Item B11, wherein said functional material is fluorescent material;

(B13) The silica particle according to Item B12, wherein said fluorescent material is rhodamine red or fluorescein;
(B14) A group of silica particles having average particle diameter adjusted in a range of nano size to micron size and having particle diameter distribution width of narrow area distribution;
(B15) The group of silica particles according to Item B14, wherein said average particle diameter is adjusted in any of 5 nm-5 µm;
(B16) The group of silica particles according to Item B14 or 15, wherein said narrow area distribution is characterized by that particle diameter distribution width is within ±250 of average particle diameter;
(B17) The group of silica particles according to anyone of Items B14-16, produced from a silica compound selected from a group consisting of mercapto-propyl-trimethoxysilane (MPS), mercapto-propyl-triethoxysilane (MPES), mercapto-propyl-methyldimethoxysilane (MPDMS), trimethoxy[2-(7-oxabicyclo[4.1.0]-hepto-3-yl)ethyl]silane (EpoPS), thiocyanatopropyltriethoxysilane (TCPS), and acryloxypropyltrimethoxysilane (AcPS);
(B18) The group of silica particles according to anyone of Items B14-17, having functional material;
(B19) The group of silica particles according to Item B18, having said functional material on surface layer of respective particles in said group of particles;
(B20) The group of silica particles according to Item B18, having said functional material inside of respective particles in said group of particles;
(B21) The group of silica particles according to anyone of Items B18-20, wherein said functional material is selected from a group consisting of fluorescent material, protein, nucleotide, oligonucleotide, sugar chain and combination thereof;
(B22) The group of silica particles according to Item B21, wherein said functional material is fluorescent material;
(B23) The group of silica particles according to Item B22, wherein said functional material is rhodamine red or fluorescein;
(B24) A standard marker including the silica particles according to Items B1-13 or the group of silica particles according to Items B14-23;
(B25) The standard marker according to Item. B24 for use in flow cytometry;
(B26) The standard marker according to Item B24, used for size marker application or beads assay application.
(B27) A production method of a silica particle or a group of silica particles, comprising: a step for producing a mixture by mixing silica compound and ammonia water; and a step for reacting the mixture in a temperature range of 80-100° C. for 2-12 hours;
(B28) The production method according to Item. B26, wherein the step for producing a mixture by mixing said silica compound and ammonia water is performed in the presence of isopropanol;
(B29) The production method according to Item B26 or 27, wherein particle diameter of said silica particle or average particle diameter of said group of silica particles is adjusted to any of 5 nm-5 µm;
(B30) The production method according to Item B28, wherein particle diameter or average particle diameter is controlled by concentration of said silica compound;
(B31) The manufacturing method according to any one of Items B26-29, wherein said silica compound is selected from a group consisting of mercapto-propyl-trimethoxysilane (MPS), mercapto-propyl-triethoxysilane (MPES), mercapto-propyl-methyldimethoxysilane (MPDMS), trimethoxy[2-(7-oxabicyclo[4.1.0]-hepto-3-yl)ethyl]silane (EpoPS), thiocyanatopropyltriethoxysilane (TCPS), and acryloxypropyltrimethoxysilane (AcPS);
(B32) The production method according to any one of Items B26-30, wherein said temperature is in a range of 90-100° C.;
(B33) The production method according to any one of Items B25-30, further comprising a step for providing a functional material to silica particle in order to produce a silica particle having a functional material on surface layer or inside;
(B34) The production method according to Item B31, wherein said functional material is selected from a group consisting of fluorescent material, protein, nucleotide, oligonucleotide, sugar chain and combination thereof;
(B35) The production method according to Item B32, wherein said functional material is fluorescent material;
(B36) The production method according to Item B33, wherein said functional material is rhodamine red or fluorescein;
(B37) A support including the silica particle according to any one of Items B1-11 or the group of silica particles according to any one of Items B12-22; and
(B38) The support according to Item B36, used for synthesis of nucleic acid or protein, or cell float culture application.

(Silica Particle of the Present Invention)

Further, the silica particle relating to the present invention, surface layer, surface and production method thereof have the following nonconventional features or characteristics with regard to effects:

(a) Features Of Surface Layer Or Surface Of Silica Particle Are as follows:
  (1) Adsorptive capacity of protein, nucleic acid or the like is high due to surface layer or acceptor group on surface;
  (2) Antigen, antibody, enzyme or the like can efficiently bind to the surface while maintaining functions thereof, without causing denaturalization (deactivation of activity and function) thereof;
  (3) Antigen-antibody reaction is possible on the surface layer;
  (4) A substance can be detected with high-sensitivity on the surface of silica particle; and
  (5) Protein, nucleic acid, dye or the like can bind to surface layer of a chemical substance by conjugate reagent.

(b) Features of silica particle itself are as follows:
  (1) Agglomeration attributable to preparation of particles and surface modification is less; and
  (2) Particle diameter of silica particles can be adjusted and regulated from nano size to micron size.

(c) Characteristics of the production method are as follows:
  (1) Number of days required for producing a silica particle is extremely short (1-12 hours) as compared with conventional method (several days);
  (2) Yield exceeds 30%; wherein the yield has been determined by measuring dry weight of a group of particles finally obtained based on the weight of silica compound before reaction start. For example, if weight of MPS is 30 mg, and dry weight of particle prepared is 10 mg, the yield is set to 10 mg/30 mg=0.33, namely, 33.3%.
  (3) The number of types of reagents required for production is less (surfactant, hydrochloric acid or the like are not used), mass production is possible by production process with one reaction stage or one reaction step; the number of container, tube, flask, tank or the like required for production is, depending on production scale, one. For example, fluorescent dye-containing silica particle of the present invention completes a reaction in one stage, different from conventional dye-containing particle. In regard to difference of progression of the reaction, with conventional routine method (A), as a first reaction, silica compound aminopropyl trimethoxysilane (APS) having amino group (a) and NHS bound dye obtained by binding of NHS reactive with amino acid and dye (b) are reacted to produce APS-dye conjugate (c). Then, as a second reaction, APS-dye conjugate (c) is added to particle synthesis reaction using TEOS (d) to incorporate the dye into silica particles via APS. However, different from such conventional method, with particle formation of the present invention by the silica compound having thiol group such as MPS, different from the routine method, dye-containing particles are formed by one-stage reaction. For example, the reaction can be completed in one stage by simultaneously performing a formation of MPS-dye conjugate, obtained by binding of maleimide group reactive with thiol group and dye and a particle formation reaction by MPS. That is, the reaction is showed schematically as follows:

(A) Conventional Method
1) APS (a)+NHS-Dye (b)=APS-Dye (c)
2) APS-Dye (c)+TEOS (d)=Dye-containing particle
(B) Novel Method
1) Maleimide-Dye+MPS (=(MPS-Dye)+MPS)=Dye-containing particle Effects of the Invention Added value of silica particles is enhanced through remarkable reduction in production costs of conventional silica particles, improvement of functions and quality, diversification and expansion of applications or the like. An efficient and potent means is provided for bioassay in medical care, environmental conservation or the like, qualitative tests, quantitative tests, diagnosis or the like.

BRIEF DESCRIPTION OF DRAWINGS

(In FIG. 19, green: YG1, pink: YG-0.75, light blue: YG-0.5, orange: YG-0.2). Those shown at middle portion show electron microscopic images of each particle (In FIG. 19, upper left: YG1, upper right: YG-0.75, lower left: YG-0.5, lower right: YG-0.2.

In FIG. 20, measurement results by flow cytometry using particles of the present invention (average value FCM-GeoMean, variation coefficient FCM-CV) are shown in the table at the bottom, and findings by the electron microscope are summarized (minimum particle diameter EM-min and maximum EM-max, average EM-mean, size yield EM-%, size width size). Results of flow cytometry are shown at the top. The results show that SSC of particles are detected respectively and distribution of signals can be confirmed as a peak. (In FIG. 20, green: 33-2894-6, pink: 33-2899-1, light blue: 33-2899-2, orange: 33-2909-3.) Those at middle portion show microscopic images of each particle.

Figure 1:
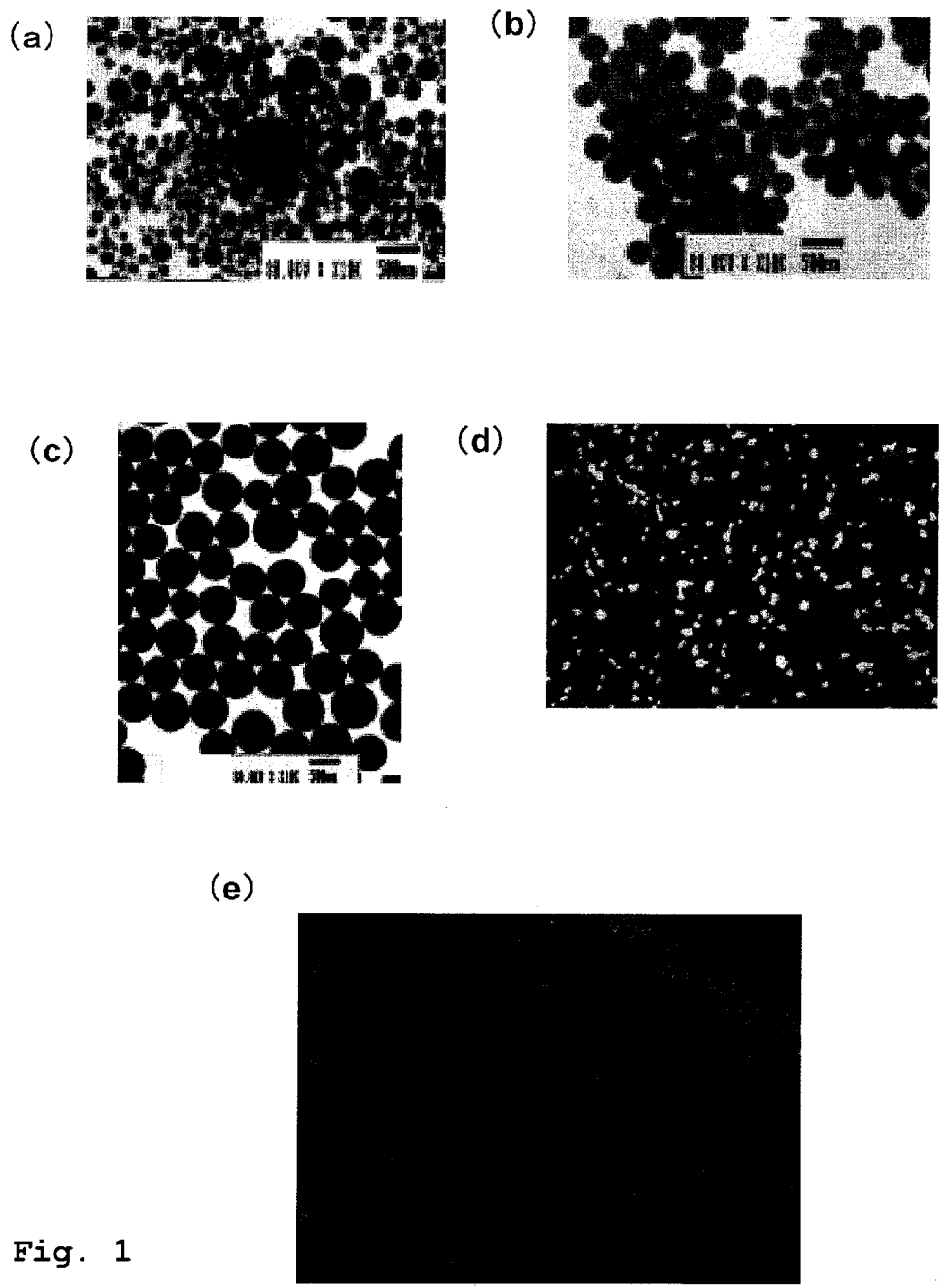
In FIG. 1, (a) is an electron microscopic image obtained in Embodiment 1, (b) is an electron microscopic image obtained in Embodiment 2, (c) is an electron microscopic image obtained in Embodiment 4, (d) is an electron microscopic image obtained in Embodiments 6-1, and (e) is a fluorescence microscopic image obtained in Embodiment 7.

BEST MODE FOR CARRYING OUT THE INVENTION (Definition of Terms)

"Nano material", "nano scale substance" or "nano substance" denotes ultrafine substance at nano scale, and normally exhibits distinguishing characters different from substances which show bulky feature in reaction against external stimulus (heat, light, voltage or the like). Examples of form of the nano scale substance include zero-dimensional structure (sphere), one-dimensional structure (needle, line), two-dimensional structure (membrane, plate), and three-dimensional structure (bulk). Examples of zero-dimensional structure include cluster, ultrafine particle, quantum dot, and dendrimer. Examples of one-dimensional structure include nano tube, nano wire, and quantum wire. Examples of two-dimensional structure include nano sheet, nano belt, nano membrane, hetero junction, and quantum well. Examples of three-dimensional structure include nano ceramics, nano metal, and nanostructure filter. Example of fine particle form of nano material includes "nano particle".

"Nano particle" is a particle with diameter of several tens nano meters. This particle is turned to cluster as a result of aggregation, reaction, growth of atoms and molecules, and stabilization and arrangement, the cluster then makes development. As used herein, the terms "silica particle", "silica sphere", "nano silica particle" or "NP" are used interchangeably, and denote particulate substance produced from "silica compound".

As used herein, "silica compound", "silane compound", "silane derivative", and "silicon compound" are used interchangeably, denote compounds composed primarily of silicon (Si) atom, intend to play a role of supply source for providing silicon to the relevant particle upon producing nano particle, are compounds provided in the form of, for example, $SiR_1R_2R_3R_4$ ($R_1$, $R_2$, $R_3$, and $R_4$ are respectively arbitrary organic group), are more preferably mercapto-propyl-trimethoxysilane (MPS), mercapto-propyl-triethoxysilane (MPES), mercapto-propyl-methyldimethoxysilane (MPDMS), trimethoxy[2-(7-oxabicyclo[4.1.0]-hepto-3-yl)ethyl] silane (EpoPS), thiocyanatopropyltriethoxysilane (TCPS), and acryloxypropyltrimethoxysilane (AcPS), and denote compounds having characteristics equivalent to physical and chemical properties thereof. As used herein, "thiol silica particle" denotes MPS nano particle, MPES nano particle or MPDMS nano particle.

In general, methods for creating nano scale substances are classified into bottom-up method and top-down method. With the former, namely, bottom-up method is a method in which atoms or molecules are interacted by physical or chemical method for scale-up purpose. Controls are possible in the order of atoms and molecules. Examples of bottom-up method include laser radiation method (membrane growth method), self-assembly method, chemical vapor deposition method, sol-gel method, coagulation-sedimentation method, and combinatorial chemistry method. Top-down method is a method in which miniaturization is performed by destroying or processing bulky substances, and examples thereof include lithography method and etching method. As nano particle synthesis, sol-gel method, gas phase method, spray method or the like are used. Among them, sol-gel method is a method in which liquid in sol state is dried to convert it to gel state and solid is synthesized (Stober, W.: Fink, A.; Bohn, E. J. Colloid Interface Sci., 1968, 26, 62-69). In order to synthesize nano particles of the present invention, sol-gel method (Stober method) is utilized. According to conventional sol-gel method, nano particles are produced at room temperature in the particle production step. "High-temperature condition" in the production method of a silica particle and a group of silica particles of the present invention means reaction condition within a temperature range of 70-100° C., preferably 80° C.-100° C., more preferably 90° C.-100° C.

"High ammonia condition" in the production method of a silica particle and a group of silica particles of the present invention means that concentration of ammonia water prepared is not less than 20% at final concentration and is preferably 20%-30%, 25%-30%, 26%-28%, more preferably 27%. In the method, medium ammonia concentration means concentration of ammonia water prepared at final concentration of not less than 10% and less than 20%. Low ammonia concentration means concentration of ammonia water prepared at final concentration of not less than 2% and less than 5%. As for "high ammonia condition", when ammonia is used in sol-gel method, several percent of ammonia concentration is used in the conventional method, and "high ammonia condition" used in the present invention is not used therein. One of reasons for that with regard to TEOS which has been used to produce nano particles is considered to be attributable to the tendency for TEOS to disfavor high-ammonia in particle formation. In fact, according to verification results obtained by the present inventors, it is determined that TEOS tends to disfavor high-ammonia in particle formation, and defective results that particles are not formed completely or agglomeration occurs are obtained (unpublished). Therefore, the fact that nano particles with unprecedented excellent characteristics could be synthesized quickly using these conditions in the production method of a silica particle of the present invention is an astonishing result.

As used herein, "lattice" and "silica network" in nano particle of the present invention are used interchangeably, and the lattice of particles represents internal structure as the primary particle and intends a stereoscopic structure in mesh form via chemical bond represented by Si—O—, Si—C—, or the like.

In one aspect, the present invention relates to "non-pored" silica particle or "without pore" silica particle.

In one embodiment, features of "non-pored" or "without pore" are such that, for example, there is no "macro pore" and there is no pore of 20 μm or more. Further, in another embodiment, non-pored silica particle of the present invention has, for example, specific surface area of 4.816 ($m^2/g$) in particles having average particle diameter of about 900 nm, and pore volume is 0.0159 ($m^3/g$). "Pore" is a term showing porous structure, and the pore is largely classified into micro pore, meso pore, and macro pore. "Micro pore" denotes pores having a diameter of not more than 2 nano meters (nm). "Meso pore" denotes pores having a diameter in a range of 2-50 nano meters (nm). Further, "macro pore" denotes pores having a diameter of 50 nano meters (nm).

"Substantially spherical" as used for particles denotes particles in spherical shape without presenting irregular structure due to that there is no pore.

"Gas adsorption method" is one of the most common means for obtaining pore distribution, specific surface area or the like. The method is performed by a specific surface area pore distribution measuring device from Beckman-Coulter. With this method, pore distribution and specific surface area can be measured based on BET theory.

As used herein, "particle diameter" is an index showing magnitude of particles of measurement target and can be expressed by the diameter of the particle. "Particle diameter" can be measured and determined by various technologies. For example, particle diameter can be determined using a transmission electron microscope.

As used herein, "size distribution" or "grain size distribution" are used interchangeably, and "size distribution" shows distribution pattern of "particle diameter" in the group of particles of measurement target. Although "size distribution"

can be measured by various technologies, size distribution of particles can be assessed using flow cytometry or the like.

As used herein, "particle diameter distribution width" is an index showing degree of dispersibility of "particle diameter" in "size distribution" and shows a width where particle diameter of target particles exists. In the present invention, one of features of particle diameter distribution width is that particle diameter distribution width in the target group of particles is of narrow area distribution within ±25% of the average particle diameter.

"Flow cytometry" is a means for optically analyzing individual particle while fine particles (for example, single cell of floating cell in sheath liquid) are dispersed in a fluid and this fluid is flown in a slender stream. Light beam with constant wavelength (normally laser light) is irradiated to the fluid, and forward scatter (FSC) in the direction along with the light beam and side scatter (SSC) in the direction perpendicular to the light beam are normally detected. In general, intensity of the forward scatter light is proportional to surface area of measurement target particle and hence is used as an index showing magnitude of fine particles thereof, and side scatter, since caused by refraction and scatter of a measurement target, can be used as an index for complication of internal structure. In the present invention, side scatter light is used for a case where positive correlation is found between particle diameter of particle family used and side scatter light.

As used herein, "size marker" denotes a substance that plays a role of giving an index for quantitative determination of size for measurement target system.

As used herein, "size yield" or "size control rate" in the size control assessment by electron microscope are used interchangeably and are defined by the following formula: "size yield"={(maximum particle diameter)−(minimum particle diameter)}/{2×(average particle diameter)}×100(%) wherein, "average particle diameter"={(maximum particle diameter)+(minimum particle diameter)}/2

These values are measured by transmission electron microscope or calculated based on measurements thereof.

As used herein, "acceptor group" denotes a functional group introduced onto silica particle or silica sphere. Relationship between silica compound used for silica particle formation and acceptor group to be introduced is, for example, in the following correspondence relationship:

TABLE 1A

| Silica compound (4) | Acceptor group formed on silica sphere surface |
|---|---|
| Tetraethoxysilane | OH group |
| γ-mercaptopropyltriethoxysilane | SH group |
| Aminopropyltriethoxysilane | $NH_2$ group |
| 3-thiocyanatopropyltriethoxysilane | SCN group |
| 3-glycidyloxypropylethoxysilane | Epoxy group |
| 3-isocyanatopropyltriethoxysilane | CNO group |

As used herein, "functional material" denotes a substance bearing physical, chemical or biological actions and its form is arbitrary as long as it has a site interacting with a target to act. Examples of functional material include medical agent, fluorescent substance, protein, peptide, nucleotide, nucleotide analog, oligonucleotide, oligonucleotide analog, and sugar chain, but not limited thereto.

As used herein, "fluorescent substance" denotes a substance that emits fluorescence when being excited by external stimulus such as electromagnetic wave (e.g., ultraviolet ray, X-ray, electron beam). Examples of "fluorescent substance" include rhodamine red, fluorescein, hexanoic acid-6-(tetramethyl rhodamine-5-carboxamide), hexanoic acid-5-(tetramethyl rhodamine-5-carboxamide), Alexa Fluor 647, DY 635, DY 485, DY 495, DY 505, and tris dichlororuthenium (II) hexahydrate, but not limited thereto. The fluorescent substance is present in silica particles in, for example, the aspects shown in (1) to (4) below, but not limited thereto. That is: (1) they are contained independently inside; (2) reaction product of one in which fluorescent substance and a compound selected from N-hydroxy succinimide (NHS) and isothiocyanate (ITC), and 3-(aminopropyl)triethoxysilane is contained inside or exists on the surface layer in a form bound to the silica network; (3) reaction product of one bound to maleimide and MPS is contained inside or exists on the surface layer in a form bound to the silica network; or (4) one in which fluorescent substance and maleimide are bound exists on the surface layer due to reaction with silica particle containing silica compound having thiol.

As used herein, "surface layer functionalization" denotes that functional materials are disposed on the surface layer of silica particle of the present invention and are stabilized. Further, properties of target particles capable of performing the surface layer functionalization is expressed as internal functionalization capability. As used herein, "to stabilize" is to provide a physically and chemically stabilized state required for that the functional material realizes a desired function with repeatability in silica particles under use environments thereof.

As used herein, "internal functionalization" denotes that functional material is contained in the silica particle of the present invention and is stabilized. Further, properties of the target particle capable of performing the internal functionalization are expressed as internal functionalization capability.

As used herein, terms "protein", "polypeptide", "oligopeptide" and "peptide" are used in the same meaning herein and denote polymer of amino acid with arbitrary length and altered body thereof. The polymer may be straight chain, branched or cyclic. The amino acid may be natural, nonnatural, or altered amino acid. This term encompasses those which could be assembled to a complex of a plurality of polypeptide chains. This term also encompasses natural or artificially altered amino acid polymer. Examples of such alterations include disulfide bonding, glycosylation, lipidation, acetylation, phosphorylation, or other arbitrary manipulation or alteration (e.g., conjugation to labeling molecule). This definition also encompasses, for example, polypeptide including one or two or more analogues of amino acid (e.g., including normatural amino acid), peptide-like compound (e.g., peptoid) and other alterations known in the art. When used in the composition of the present invention, "protein" is preferably a protein compatible with a host in which the composition should be used, but any protein may be used as long as it is processed to be compatible with the relevant host. Whether or not a certain protein has compatibility with the host, and whether or not it can be processed so as to be compatible with the host can be determined by observing if it is colonized in the host by implanting the protein to the host and suppressing, if necessary, side reaction such as immunological rejection reaction. Typically, examples of protein having compatibility as described above can include a protein derived from the host, but not limited thereto.

As used herein, "nucleotide" denotes a nucleotide where sugar part thereof is ester phosphate, which encompasses DNA and RNA, and which may be natural one or normatural one. Here, nucleotide means a compound in which base and sugar are N-glycoside-bond. "Nucleotide derivative" or "nucleotide analogue" denotes one that is different from naturally-occurring nucleotide, but has the same functions as original nucleotide. Such nucleotide derivative and nucleotide analogue are well known in the art. Examples of such nucleotide derivative and nucleotide analogue include phosphorothioate, phosphor amidate, methyl phosphonate, chiral-methyl phosphonate, 2-O-methyl ribonucleotide, peptide nucleic acid (PNA), but not limited thereto. DNA encompasses cDNA, genome DNA, synthetic DNA.

As used herein, "support" denotes a material capable of fixing a target substance. Examples of materials for the support include arbitrary solid material having characteristics binding to a substance such as biological molecule usable in the present invention in either covalent binding or noncovalent binding or can be derivatized so as to have such characteristics. Silica particle of the present invention can be utilized as the support.

Embodiments of the present invention will be explained hereinafter. First, production or preparation of MPS particle is explained.

(MPS Particle)

(a) Preparation of MPS particle with MPS and ammonia: after MPS and 28% by weight ammonia water are mixed, the mixture is stirred, kept at a temperature of 80-100° C., preferably at 95±5° C., for 1-12 hours, preferably 7±5 hours, and reacted to produce MPS particles. MPS particles produced are collected in the form of pellet by high-speed centrifugation, washed with 70% ethanol solution and distilled water by centrifugation alternately for a total 4-8 times. The pellets collected (MPS particles) are dispersed by high-speed homogenizer, ultrasonic processing or the like, and are subjected for use. Diameter of MPS particles can be adjusted and regulated from nano size to micron size according to variation of MPS concentration used for production. For example, the added amount of MPS to 28% by weight ammonia water (constant amount) can be regulated so as to obtain a desired particle diameter and appropriately varied. Table 1 in Example 3 described below shows correlationship among three items of MPS concentration with regard to 675 µl (constant amount) of 28% by weight ammonia water, average particle diameter and size yield (O).

(b) Production of MPS particles by MPS, isopropanol, and ammonia: MPS particles can be produced by mixing MPS, isopropanol, and 28% by weight ammonia water, stirring the mixture while keeping warm at a temperature 80-100° C., preferably at 95±5° C. for 1-12 hours, preferably 7±5 hours, and reacted. Collection, washing, dispersion of PMS particles thus produced are as above (a). Diameter of MPS particles can be adjusted and regulated by variation of MPS concentration used for production and alteration of I/N volume ratio [volume (I) of isopropanol solution:volume (N) of 28% by weight ammonia water]. MPS concentration and I/N ratio with regard to 28% by weight ammonia water (constant amount) can be adjusted so as to obtain a desired particle diameter and appropriately varied. Table 2 in Embodiment 5 described below shows correlationship among three items of MPS concentration with regard to 337.5 µl (constant amount) of 28% by weight ammonia water, I/N ratio and average particle diameter.

(c) Production of MPS particles containing labeling molecule: MPS-labeling molecule conjugate is prepared in advance by reacting a substance reactive with thiol group, such as maleimide compound, labeling molecule such as bound substance with rhodamine, and thiol group of MPS. Then, after the conjugate, MPS and ammonia water are mixed, or after the conjugate, MPS, ammonia water, and isopropanol are mixed, MPS particles containing the labeling molecule are produced through stirring and keeping warm as in above (a). At least one labeling molecule may be contained.

Further, it is also possible to prepare other types of silica compound-labeled molecule conjugate by using other types of silica compound, not limited to MPS. The particle diameter can be regulated by MPS concentration as described above. MPS particles thus produced are presented for use after collection, washing and dispersion. Concrete examples are shown in Embodiment 7 described below.

Next, applications of silica particles of the present invention will be explained.

(d) Labeled body for qualitative test, quantitative test, and diagnosis: the labeled body used herein denotes a silica particle in a state where a labeling substance is embedded, included, contained, adsorbed or bound in MPS particle or other silica particle described in the present specification, surface layer, surface or the like. For the labeling substance, substance used for detection in qualitative tests, quantitative tests, diagnosis, bioassay or the like and marker for reaction, for example, fluorescent material, luminescent material, biologically active agent, functional material, immunological reactive material, gene or the like, which are known substances, may be used. More specific examples thereof can include FITC, enzyme, hormone, TNF, antigen, antibody, cytokine, ligand, receptor, toxin, TLR, DNA, and RNA. Meanwhile, MPS particle labeled by single substance may be used as mono labeled body, and MPS particle labeled by a plurality of substance may be used as poly labeled body or barcode substance.

(e) Tools for qualitative tests, quantitative tests, and diagnosis: tools used herein denote slide glass, microchip, tray or the like in which surface of substrate thereof comprises immobilized MPS particles, and which may be labeled, before use, by various labeling substances described in above (d) via immobilized MPS particles.

(f) Support for synthesis and modification of protein, nucleic acid, and enzyme: the support used herein means that peptide chain, DNA and RNA fragment, active center of enzyme, epitope, or the like is adsorbed or bound on MPS particle surface, and the resultant may be modified, elongated, synthesized, subjected to PCR or the like in this state (MPS particles are used as the support).

(g) Medium for adsorption and/or elution of mixed substances for purification: the medium used herein denotes a purification means for removal of impurities by binding or adsorption via, for example, thiol group on MPS particle surface. Further, if antigen is bound onto MPS particle surface, it may be used as medium for antigen purification.

(h) Slow-release substance and carrier of drug delivery system (DDS): if, for example, a drug is contained in MPS particle, it functions as drug slow-release substance, and if an organ specific antigen is bound onto surface of the slow-release substance MPS particle, it may be used as the organ specific drug slow-release substance (for missile therapy).

(i) Noninfectious particle tracer, scintillator

If, for example, antigen of infectious factor is bound to MPS particle surface, it may be presented to researches as noninfectious factor without nucleic acid. Further, if fluorescent dye, RI compound, and the like are contained in MPS particles, it may be used as tracer and scintillator. Further, by adding aforementioned slow-release substance and carrier functions of DDS thereto, it may be used as therapeutic agent or agent for both of diagnosis and therapy capable of performing assessment and confirmation as well as therapy of the delivery at the same time.

(j) Fluorescent standard marker for flow cytometry

For example, fluorescent substance is incorporated into MPS particle inside, or luminescent material is bound to particle surface, it may be presented as particle for beads assay for flow cytometry or fluorescent standard marker.

(k) Support for cell float culture

For example, MPS particle may be used as the support for anchorage of cells in cell float culture.

As mentioned above, mercaptopropyltrimethoxysilane (MPS) particles of the present invention have useful characteristics and develop remarkable effects due to these characteristics as compared with conventional silica particles, while silica particles having features of the present invention can also be prepared from at least one silica compound selected from a group consisting of mercapto-propyl-triethoxysilane (MPES), mercapto-propyl-methyldimethoxysilane (MP-DMS), trimethoxy[2-(7-oxabicyclo[4.1.0]-hepto-3-yl)ethyl] silane (EpoPS), thiocyanatopropyltriethoxysilane (TCPS), and acryloxypropyltrimethoxysilane (AcPS).

Hereinafter, configurations and effects of the present invention will be explained in detail referring to comparative examples and examples. However, the present invention is not limited only to reference examples and examples.

EXAMPLES

Comparative Example 1

Preparation of TEOS Particle

To 125 µl of water were added 500 µl of ethanol, 7.5 µl of TEOS, 50 µl of 27% by weight ammonia water, and stirred and reacted at room temperature for 24 hours. Subsequently, the reaction completed solution was loaded to high-speed centrifugal machine (10,000×g, 5 minutes), and pellets were collected therefrom. The pellets thus obtained were washed repeatedly with 70% by volume ethanol and distilled water by centrifugation alternately 3 times, total 6 times. Next, pellets after washing (produced silica particles) were stirred by the ultrasonic crushing machine and dispersant TEOS particles were obtained.

Example 1

Preparation of Silica Particles by MPS

To 125 µl of water were added 500 µl of ethanol, 7.5 µl of MPS, 50 µl of 28% by weight ammonia water, mixed, and reacted at room temperature for 48 hours. Subsequently, the reaction completed solution was loaded to high-speed centrifugal machine (10,000×g, 5 minutes), and pellets were collected therefrom. The pellets thus obtained were washed repeatedly with 70% by volume ethanol and distilled water by centrifugation alternately 3 times, total 6 times. Next, pellets after washing (silica particles) were stirred by the ultrasonic crushing machine, sampled, and observed by the electron microscope. As a result, formation of nano silica particles was confirmed.

Example 2

Preparation of Silica Particles with Average Particle Diameter of not More than 500 Nm (Size Control Rate: Within ±200)

To 7.5 µl of MPS was added 675 µl of 28% by weight ammonia water, mixed, and reacted at 90° C. for 9 hours. Subsequently, the reaction completed solution was loaded to high-speed centrifugal machine (10,000×g, 5 minutes), and pellets were collected therefrom. The pellets thus obtained were washed repeatedly with 70% by volume ethanol and distilled water by centrifugation alternately 3 times, total 6 times. Next, pellets after washing (silica particles) were stirred by the ultrasonic crushing machine, sampled, and observed by the electron microscope. As a result, average particle diameter of silica particles was 360 nm and size control rate thereof was about 190, and preparation of silica particles under good size control was thus confirmed.

Example 3

Regulation of Silica Particle Diameter by Variation in Amount of MPS

Adjustments and regulations of silica particle diameter were carried out by varying the amount of used MPS for 675 µl (constant amount) of 28% by weight ammonia water. Silica particles (MPS particles) were produced with a similar manner as in Example 2 except for the variation in amount of MPS. Results are shown in Table 1. Particle diameter increased as MPS concentration increased. In other words, positive correlation was found between MPS concentration and particle diameter.

TABLE 1

|  | MPS concentration (mM) | | | | |
|---|---|---|---|---|---|
|  | 114 | 57 | 19 | 6.3 | 2.1 |
| Average particle diameter (nm) | 475 | 360 | 265 | 45 | 20 |
| Size yield (%) | 13 | 19 | 17 | 13 | 19 |

Example 4

Preparation of Silica Particle with Average Particle Diameter of not Less than 400 Nm (Size Control Rate: Within ±200)

To 15 µl of MPS were added 337.5 µl of isopropanol solution and 337.5 µl of 28% by weight ammonia water, mixed, and reacted at 95° C. for 3.5 hours. Subsequently, the reaction completed solution was loaded to high-speed centrifugal machine (10,000×g, 5 minutes), and pellets were collected therefrom. The pellets thus obtained were washed repeatedly with 70% by volume ethanol and distilled water by centrifugation alternately 3 times, total 6 times. Next, pellets after washing (silica particles) were stirred by the ultrasonic crushing machine, sampled, and observed by the electron microscope. As a result, average particle diameter of silica particles was 750 nm and size control rate thereof was about 16%, and preparation of silica particles under good size control was thus confirmed.

Example 5

Regulation of Silica Particle Diameter by Changes in Variation in an Amount of MPS and I/N Ratio Silica particles were prepared with a similar manner as in Example 4 except for variation of amount of used MPS for ammonia water (constant amount) and alteration of I/N volume ratio [volume of isopropanol solution (I):volume (N) of 28% by weight ammonia water]. Results are shown in Table 2. Positive correlation was found between amount of used MPS (concentration) for ammonia water (constant amount)

and particle diameter. Meanwhile, no definite correlation was found between I/N ratio and particle diameter.

TABLE 2

| | MPS concentration (mM) | | | | | |
|---|---|---|---|---|---|---|
| | 228 | 114 | 114 | 76 | 57 | 57 |
| I:N | 7.5:2.5 | 7.5:2.5 | 5:5 | 7:3 | 7:3 | 5:5 |
| Average particle diameter (nm) | 1315 | 805 | 750 | 635 | 555 | 490 |
| Size yield (%) | 8 | 15 | 16 | 13 | 17 | 16 |

Example 6

Example 6-1

Preparation of Silica Particle Containing Rhodamine

As shown below, (a) silica compound containing rhodamine (labeling molecule) was prepared in advance, and (b) silica sphere containing rhodamine (labeling molecule) was prepared using the silica compound obtained.
(Preparation of (a) Silica Compound Containing Rhodamine (Labeling Molecule)

As maleimide compound, Rhodamine Red™ C2 maleimide (about 5 mg) was dissolved into 50 µl of DMSO solution, (3-mercaptopropyl)-trimethoxysilane, which has a thiol group, was added and mixed to be equimolar to the Rhodamine Red™ C2 maleimide, stirred using a tube mixer under light shielding for 2 hours and reacted to prepare silica compound containing rhodamine (labeling molecule), and (presented to the following (b) preparation of silica spheres.)

(b) Preparation of Silica Spheres Containing Rhodamine Labeling Molecule

To 7 µl of reaction solution containing silica compound containing rhodamine (labeling molecule) obtained in above (a) was added 7.5 µl of MPS and about 675 µl of 27% by weight ammonia water, mixed, and reacted at 100° C. for about 11 hours. Subsequently, the reaction completed solution was loaded to high-speed centrifugal machine (10,000× g, 5 minutes), and pellets were collected therefrom. The pellets were washed with 70% by volume ethanol and distilled water alternately. Washing was performed repeatedly by centrifugation for total 6 times. Pellets collected (silica particle) were stirred and dispersed by the ultrasonic crushing machine, sampled, and observed by fluorescence microscope, and it was confirmed that particles emitted fluorescence of rhodamine.

This confirmation means that the present invention has very useful characteristics as compared with conventional art. Namely, one obtained by binding of N-hydroxy succinimide ester reactive with amino acid and fluorescent dye and amino group of APS were reacted to form APS-fluorescent dye conjugate, it was then mixed when preparing silica particle with the resultant and TEOS or the like, and with silica particle containing fluorescent dye, amino group (positive charge) of unreacted APS was neutralized with Si—O— (negative charge) of silica, and particle agglomeration occurred due to reduction in surface charge of the particles, while in the present example, MPS-fluorescent dye conjugate was formed by reaction of one obtained by binding of maleimide reactive with thiol group and fluorescent dye, and thiol group of MPS, it was then mixed when preparing silica particle using the resultant and MPS, and MPS silica particle containing fluorescent dye could be prepared without causing agglomeration.

Example 6-2

Preparation Method of Silica Particles Containing Dye by One-Stage Reaction

10 µl of 3.4M 3-mercaptopropyltriethoxysilane, 5 µl of 10 mM Rhodamine Red™ C2 maleimide, 245 µl of isopropanol solution, and 245 µl of 28% by weight ammonia water were mixed, and reacted at 100° C. for 3 hours. The solution obtained (reaction completed solution) was washed repeatedly total 6 times. Pellets collected (silica particle) were stirred and dispersed by the ultrasonic crushing machine, sampled, and observed by the fluorescence microscope, and it was confirmed that particles emitted fluorescence of rhodamine.

Example 7

Surface Layer Functionalization by Fluorescent Dye Labeling of MPS Particle (1) Preparation of MPS Particles
To 10 µl of MPS were added 405 µl of isopropanol solution and 290 µl of 28% by weight ammonia water, mixed and reacted at 95° C. for 2 hours. Subsequently, the reaction completed solution was loaded to high-speed centrifugal machine (10,000×g, 5 minutes), and pellets were collected therefrom. The pellets were washed with 70% ethanol and distilled water alternately. Washing was performed repeatedly by centrifugation for total 6 times. Pellets collected (silica particle) were stirred and dispersed by the ultrasonic crushing machine, sampled, and observed by the fluorescence microscope, and it was confirmed that average particle diameter was 690 nm and size control rate was about 150, and preparation of particles under good size control was thus confirmed.
(2) Functionalization by Surface Layer Labeling of Rhodamine (Labeling Molecule)

As maleimide compound, Rhodamine Red™ C2 maleimide (5 mg) was dissolved into 73.5 µl of DMSO solution, 3 µl of MPS particle solution prepared in above (1) was added, stirred and reacted with the tube mixer under light shielding for about 2 hours. Subsequently, the reaction completed solution was loaded to high-speed centrifugal machine (10,000× g, 5 minutes), and pellets were collected therefrom. The pellets were washed repeatedly with 70% ethanol and distilled water alternately. Washing was performed repeatedly by centrifugation for total 6 times. Pellets collected (silica particle) were stirred and dispersed by the ultrasonic crushing machine, sampled, and observed by the fluorescence microscope, and it was confirmed that particles emitted fluorescence of rhodamine. That is, preparation of surface layer functionalized MPS particle by rhodamine (labeling molecule) surface layer labeling succeeded.

Example 8

<Purpose> Protein Adsorptive Capacity of MPS Nano Silica Particles on Glass Substrate is Assessed <Method>
(a) Each 0.2 µl of MPS silica particle and TEOS silica particle were spotted onto a glass substrate and dried.
(b) 2 µl of 7.5 µg/ml Cy3 labeled anti-goat antibody IgG (from Jackson Corp.) was dropped, reacted in a moist chamber at room temperature for 5 minutes, and washed.
(c) Fluorescence intensity of each spot was measured by fluorescence image analyzer (TAKARA FM BIO II).

\<Results> Fluorescence intensities of no particle spot (−), MPS nano silica particle, and TEOS nano silica particle were 8,871, 32,743, and 12,751, respectively, and it was proven that MPS nano silica particle could adsorb, hold and significantly immobilize proteins.

Example 9

\<Purpose> to Perform Bioassay on Glass Plate with Nano Silica Particle Mediation Method \<Method> (a) 0.2 µl of MPS silica particle was spotted on the glass substrate and dried; (b) 2 µl of goat GST antibody (from Amersham Corp.) of various concentrations (10 ng/ml-30 µg/ml) was dropped on spots of silica particle, reacted in a moist chamber at room temperature for 5 minutes, and washed; (c) using PBS solution containing 1% BSA, blocking reaction was performed in the moist chamber at room temperature for 10 minutes and washed; (d) using 7.5 µg/ml of Cy3 labeled anti-goat antibody IgG (from Jakson Corp.), reaction was performed in the moist chamber at room temperature for 1 hour, and washed; (e) fluorescence intensity of each spot was measured by fluorescence image analyzer (TAKARA FM BIO II).
\<Results> Concentration dependence of fluorescence intensity could be confirmed with goat anti-GST antibody in 30 ng/ml-30 µg/ml. Goat antibody could be detected in broader concentration range by the nano silica mediation method when it was immobilized on the glass plate while holding antigenecity of goat antibody.

Example 10

\<Purpose> To Perform Bioassay on Glass Plate with Nano Silica Particle Mediation Method \<Method>
(a) 0.2 µl of MPS silica particle was spotted on the glass substrate and dried; (b) 1 µl of purified enzyme GST was dropped on spots of silica particle, reacted in the moist chamber at room temperature for 5 minutes, and washed; (c) using PBS solution containing 1% BSA, blocking reaction was performed in the moist chamber at room temperature for 10 minutes and washed; (d) 2 µl of goat anti-GST antibody (from Amersham Corp.) of various concentrations (10 ng/ml-30 µg/ml) was dropped, reaction was performed in the moist chamber at room temperature for 1 hour, and washed; (e) reaction was performed with Cy3 labeled anti-goat anti-IgG (7.5 µg/ml) in the moist chamber at room temperature for 1 hour, and washed; (f) fluorescence intensity of each spot was measured by fluorescence image analyzer (TAKARA FM BIO II).
\<Results> Concentration dependence of fluorescence intensity could be confirmed with goat anti-GST antibody in 300 ng/ml-30 µg/ml. Binding of anti-GST antibody could be detected in various concentrations when it was immobilized on the glass plate while holding antigenecity of GST by nano silica mediation method.

Example 11

\<Purpose> To Perform Bioassay on Glass Plate with Nano Silica Particle Mediation Method \<Method> (a) 0.2 µl of MPS silica particle was spotted on the glass substrate and dried; (b) 2 µl of goat anti-GST antibody (from Amersham Corp.) of various concentrations (10 ng/ml-30 µg/ml) was dropped on spots of silica particle, reacted in the moist chamber at room temperature for 5 minutes, and washed; (c) blocking reaction was performed with PBS solution containing 2% skim milk in the moist chamber at room temperature for 10 minutes, and then washed; (d) reaction was performed with rhodamine labeled purified enzyme GST in the moist chamber at room temperature for 1 hour, and then washed; (e) fluorescence intensity of each spot was measured by fluorescence image analyzer (TAKARA FM BIO II).
\<Results> Concentration dependence of fluorescence intensity by rhodamine labeled GST could be confirmed with goat anti-GST antibody in 3-30 µg/ml. The antigen could be detected when it was immobilized on the glass plate while binding activity to antigen of GST antibody is held by nano silica mediation method.

Example 12

Utilization of MPS Particle as Fluorescent Standard Beads

Figure 2:
In FIG. 2, (a) is a fluorescence microscopic image of fluorescent silica particles of the present invention. Here, 10 µl of 3.4 M 3-mercaptopropyl triethoxysilane, 5 µl of 10 mM Rhodamine Red™ C2 maleimide, 245 µl of isopropanol solution, 245 µl of 28% by weight ammonia water were mixed and reacted at 100° C. for 3 hours. The resultant solution (reaction completed solution) was repeated a total of six times. Pellets (silica particles) collected were subjected to stirring and dispersion by an ultrasonic crushing machine, sampled and observed under the fluorescence microscope, and confirmed that particles emitted fluorescence. (b) shows results of flow cytometry in Embodiment 12.
Figure 2:
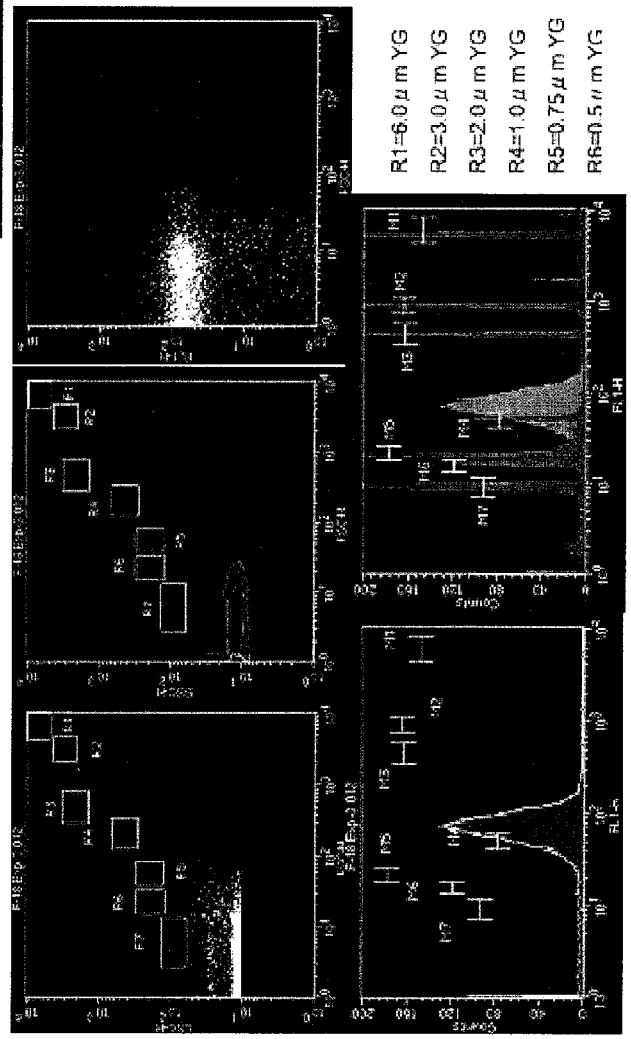
Figure 3:
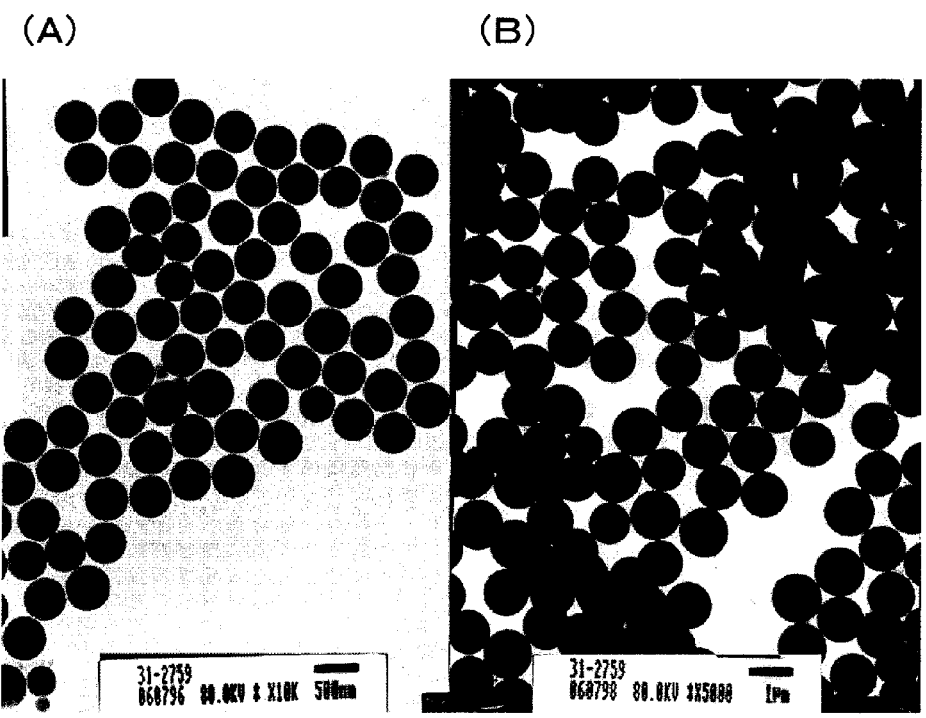
FIG. 3 shows electron microscopic image of particles containing thiol derived from MPES. (A) shows a result of observation of silica spheres by the electron microscope, obtained such that 10 µl of 3-mercaptopropyl triethoxysilane and 990 µl of 28% by weight ammonia water were mixed and reacted at 100° C. for 3 hours, the resultant solution (reaction completed solution) was subjected to centrifugal sedimentation by a high-speed centrifugal machine (10,000×g; 5 minutes), pellets thus obtained were washed with 70% ethanol and distilled water repeatedly for several times, and particles subjected to centrifugal sedimentation were stirred by the ultrasonic crushing machine. Particles with average particle diameter of 515 nm and size control rate of about 16% were prepared. (B) shows a result of observation of silica spheres by the electron microscope, obtained such that 10 µl of 3-mercaptopropyl triethoxysilane, 445 µl of isopropanol solution, and 445 µl of 28% by weight ammonia water were added and mixed, and reacted at 100° C. for 3 hours, the resultant solution (reaction completed solution) was subjected to centrifugal sedimentation by the high-speed centrifugal machine (10,000×g; 5 minutes), pellets thus obtained were washed with 70% ethanol and distilled water repeatedly for several times, and particles subjected to centrifugal sedimentation were stirred by the ultrasonic crushing machine. It was confirmed that particles with average particle diameter of 1130 nm and size control rate of about 13% were prepared.
Figure 4:
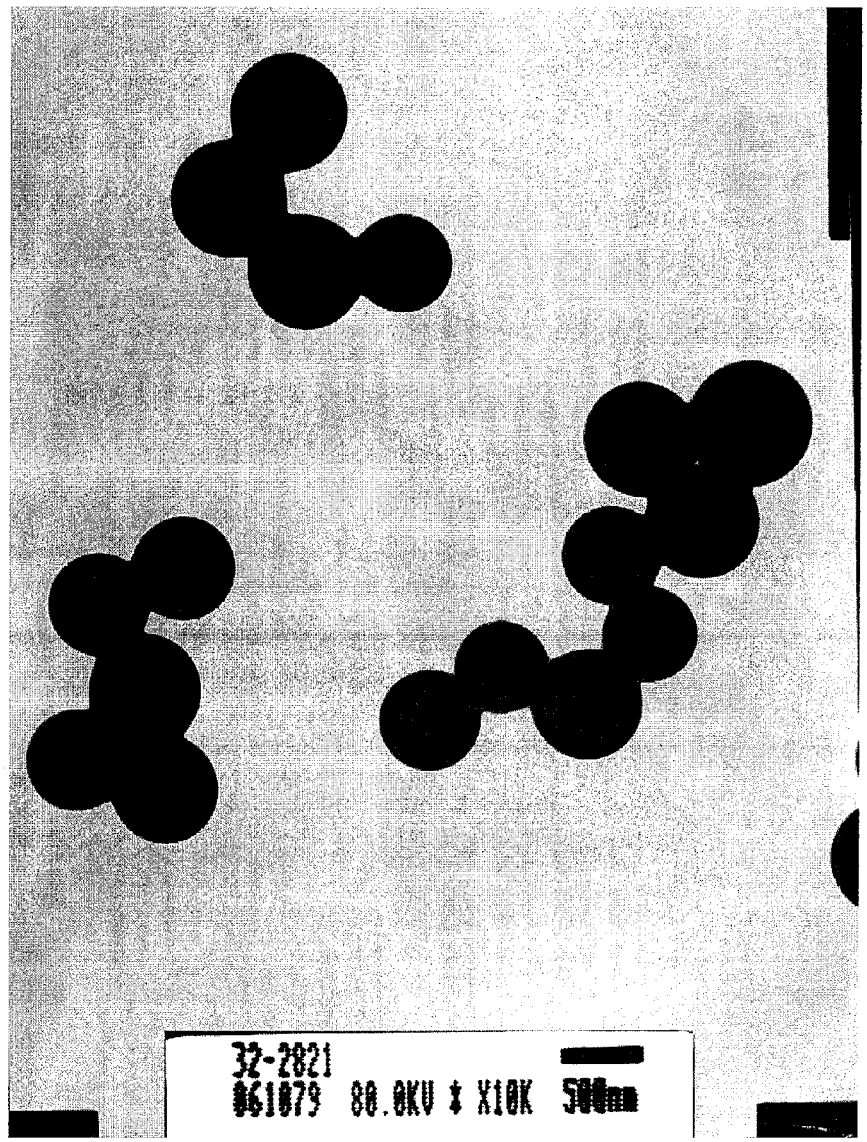
FIG. 4 shows electron microscopic image of particles containing thiol derived from MPDMS. It shows a result of observation of silica spheres by the electron microscope, obtained such that 28% by weight ammonia water was added to 10 µl of (3-mercaptopropyl)methyl dimethoxysilane to give 1 ml, mixed, reacted at 25° C. for 3 days, the resultant solution (reaction completed solution) was subjected to centrifugal sedimentation by the high-speed centrifugal machine (10,000×g; 5 minutes), pellets thus obtained were washed with 70% ethanol and distilled water repeatedly for several times, and particles subjected to centrifugal sedimentation were stirred by the ultrasonic crushing machine. It was confirmed that particles with average particle diameter of 750 nm and size control rate of about 16% were prepared.
Figure 5:
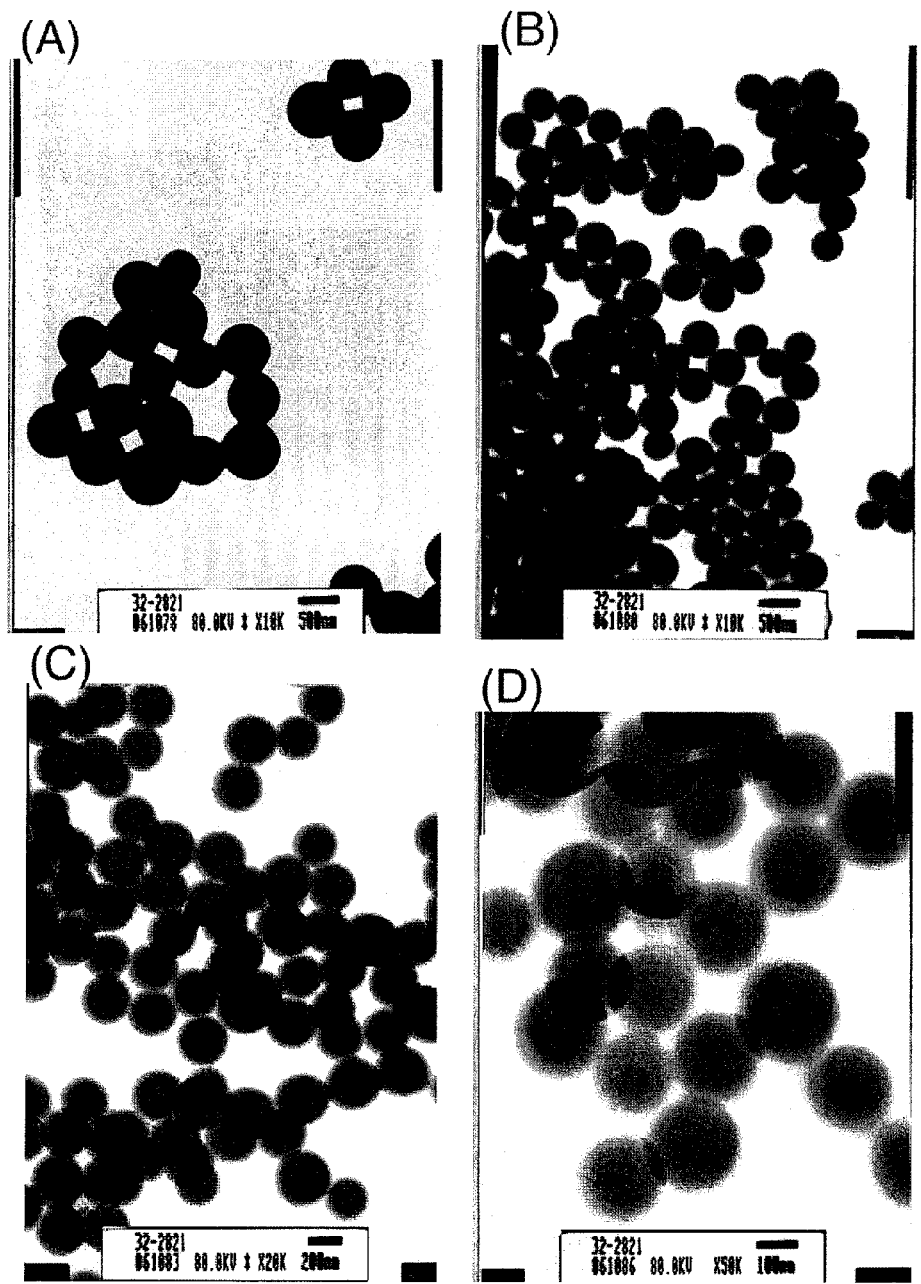
FIG. 5 shows electron microscopic image of particles containing thiol derived from MPDMS (Embodiment 3).
Figure 6:
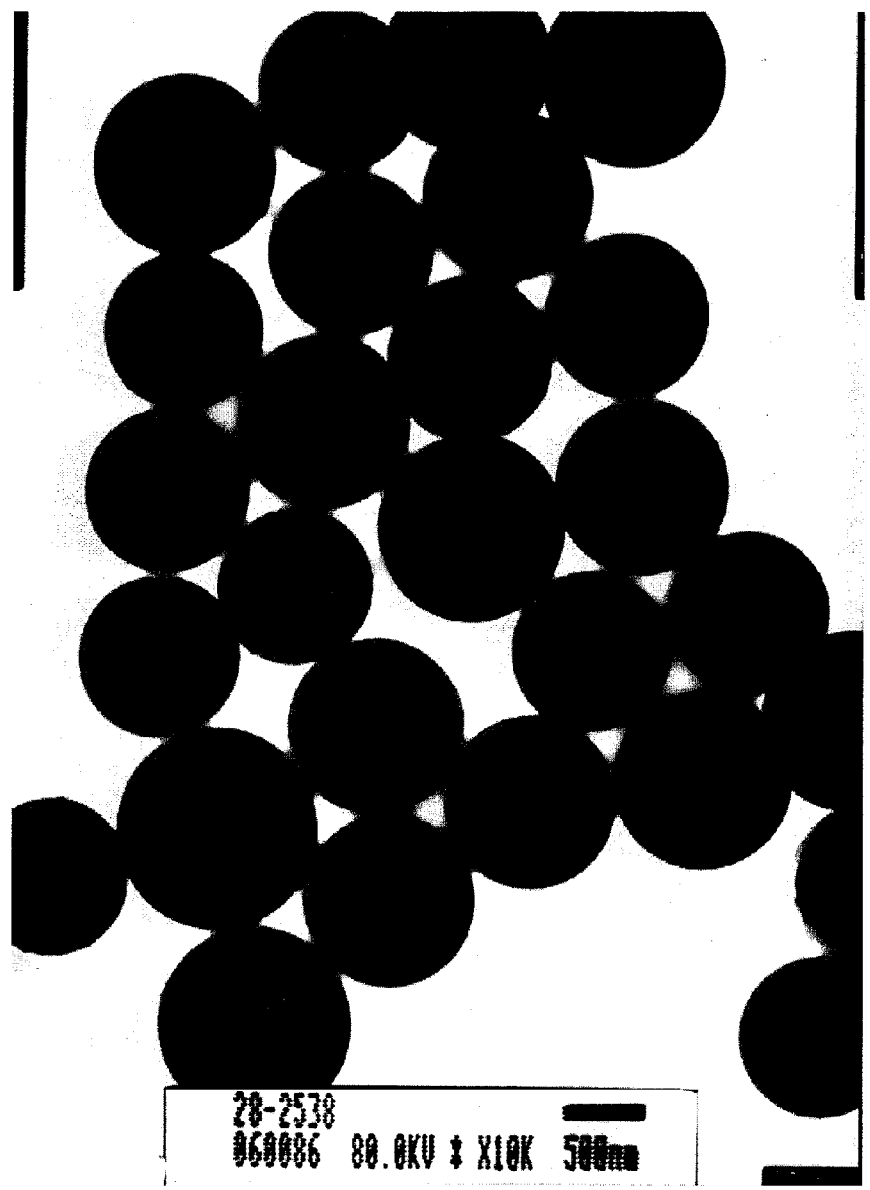
FIG. 6 shows electron microscopic image of silica particles by EpoPS. It shows a result of observation of silica spheres by the electron microscope, obtained such that 7.5 of trimethoxy [2-(7-oxabicyclo[4.1.0]-hepto-3-yl)ethyl]silane (EpoPS, (2-(3,4-epoxycyclohexyl)-ethyltrimethoxysilane)) and 675 of 28% by weight ammonia water were mixed and reacted at 95° C. for 3 hours, the resultant solution (reaction completed solution) was subjected to centrifugal sedimentation by the high-speed centrifugal machine (10,000×g, 5 minutes), pellets thus obtained were washed with 70% ethanol and distilled water repeatedly for several times, and particles subjected to centrifugal sedimentation were stirred by the ultrasonic crushing machine. It was confirmed that particles with average particle diameter of 1160 nm and size control rate of about 10.3% were prepared.
Figure 7:
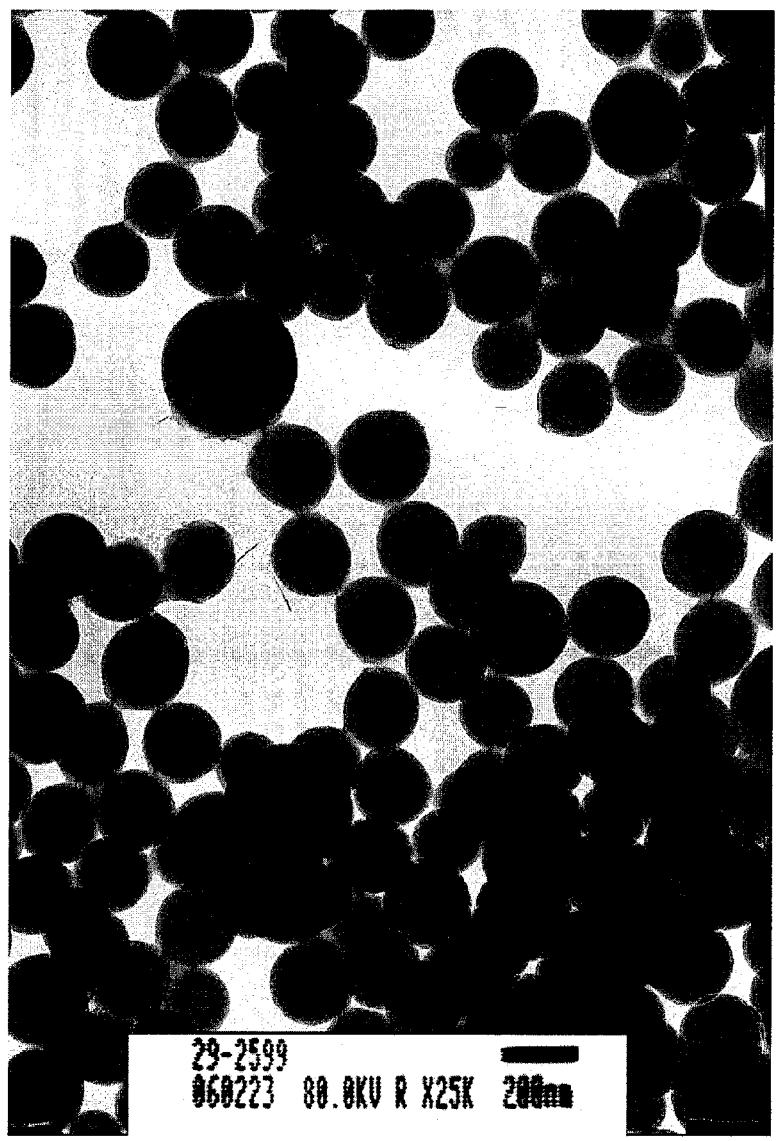
FIG. 7 shows electron microscopic image of silica particles by TCPS. It shows a result of observation of silica spheres by the electron microscope, obtained such that 7.5 µl of 3-thiocyanatopropyl triethoxysilane (TCPS) and 675 µl of 28% by weight ammonia water were mixed, reacted at 99° C. for 3 hours, the resultant solution (reaction completed solution) was subjected to centrifugal sedimentation by the high-speed centrifugal machine (10,000×g, 5 minutes), pellets thus obtained were washed with 70% ethanol and distilled water repeatedly for several times, and particles subjected to centrifugal sedimentation were stirred by the ultrasonic crushing machine. It was confirmed that particles with average particle diameter of 296 nm and size control rate of 35.1% were prepared.
Figure 8:
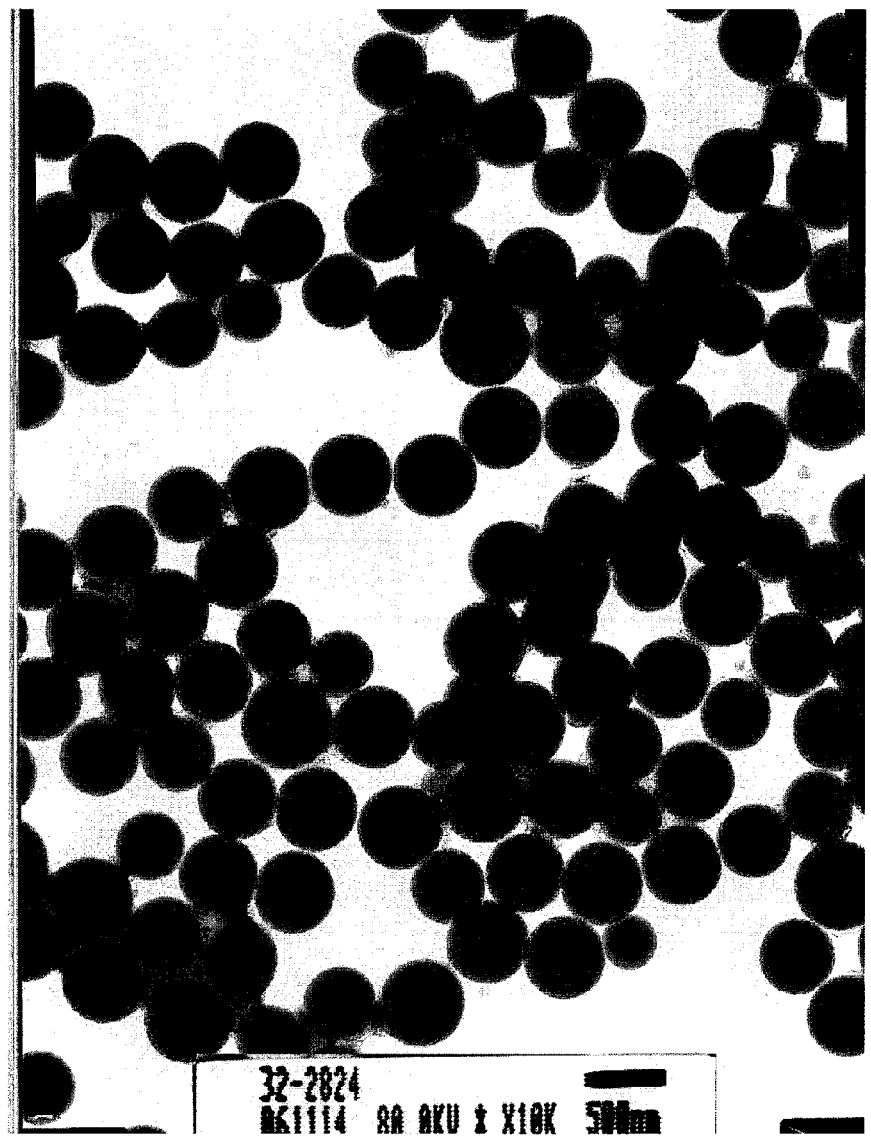
FIG. 8 shows electron microscopic image of particles containing thiol derived from AcPS. 28% by weight ammonia water was added to 10 µl of 3-acryloxypropyltrimethoxysilane (AcPS) to give 1 ml and reacted at 25° C. for 3 days. The resultant solution (reaction completed solution) was subjected to centrifugal sedimentation by the high-speed centrifugal machine (10,000×g, 5 minutes), and pellets thus obtained were washed with 70% ethanol and distilled water repeatedly for several times. Particles subjected to centrifugal sedimentation were stirred by the ultrasonic crushing machine, and these silica spheres were observed under the electron microscope. It was confirmed that particles with average particle diameter of 540 nm and size control rate of about 18.5% were prepared.

To 2.7 µl of reaction solution containing silica compound (fluorescein-APS) containing 5 mM fluorescein (labeling molecule) were added 1 µl of MPS and about 675 µl of 27% by weight ammonia water, and reacted at 100° C. for about 10 hours. Subsequently, the reaction completed solution was loaded to high-speed centrifugal machine (10,000×g, 5 minutes), and pellets were collected therefrom. The pellets were washed with 70% ethanol and distilled water alternately. Washing was performed repeatedly by centrifugation for total 6 times. Pellets collected (silica particle) were stirred and dispersed by the ultrasonic crushing machine, and particles (average particle diameter 96 nm) were obtained. These silica spheres were measured and assessed by flow cytometry FACS Calibur HG. As a result, fluorescence due to MPS particles was confirmed in the form of a clear group and peak (purple (lower left) and light green (lower right): upper left of FIG. 2 (b) is referenced for the both). Fluoresbrite supplied by Polysc ence was used as the size marker. The peak Ml in the figure (lower right) corresponds to size R1=6.0 µm. In the present example, fluorescence of fluorescent nano silica particles as extremely small as average particle diameter of about 100 nm was successfully detected. Further, as for fluorescence intensity, the peak was located between M4 and M3 of Fluoresbrite, i.e., between fluorescent peaks of 1.0 µm and 2.0 µm particles, thereby indicating that the present particle emits fluorescence intensity equivalent to Fluoresbrite of about 10-fold size. It is considered the result thus obtained a result obtained by incorporating dyes by non-pored particles in high density.

Example 13

Preparation of Thiol-Containing Particle Derived from MPES (A) 10 µl of 3-mercapto-propyltriehtoxysilane (MPES) and 990 of 28% by weight ammonia water were mixed, and reacted at 100° C. for 3 hours. The solution thus obtained (reaction completed solution) was subjected to centrifugal sedimentation by the high-speed centrifugal machine (10,000×g; 5 minutes), pellets thus obtained were washed with 70% ethanol and distilled water repeatedly for several times. Particles subjected to centrifugal sedimentation were stirred by the ultrasonic crushing machine, these silica spheres were observed by the electron microscope, and it was confirmed that particles with average particle diameter of 515 nm and size control rate of about 16% were prepared.

(B) 10 μl of 3-mercapto-propyltriehtoxysilane (MPES) and 445 μl of isopropanol solution, and 445 μl of 28% by weight ammonia water were added and mixed, and reacted at 100° C. for 3 hours. The solution thus obtained (reaction completed solution) was subjected to centrifugal sedimentation by the high-speed centrifugal machine (10,000×g; 5 minutes), pellets thus obtained were washed with 70% ethanol and distilled water repeatedly for several times. Particles subjected to centrifugal sedimentation were stirred by the ultrasonic crushing machine, these silica spheres were observed by the electron microscope, and it was confirmed that particles with average particle diameter of 1130 nm and size control rate of about 13% were prepared.

Example 14

Preparation of Thiol-Containing Particle Derived from MPDMS (A) To 10 μl of (3-mercapto-propyl)methyldimethoxysilane (MPDMS) was added 28% by weight ammonia water to give 1 ml, mixed and reacted at 25° C. for 3 days. The solution thus obtained (reaction completed solution) was subjected to centrifugal sedimentation by the high-speed centrifugal machine (10,000×g; 5 minutes), pellets thus obtained were washed with 700 ethanol and distilled water repeatedly for several times. Particles subjected to centrifugal sedimentation were stirred by the ultrasonic crushing machine, these silica spheres were observed by the electron microscope, and it was confirmed that particles with average particle diameter of 750 nm and size control rate of about 16% were prepared.

Example 15

Preparation of Silica Particles by EpoPS 7.5 μl of trimethoxy[2-(7-oxabicyclo[4.1.0]-hepto-3-yl)ethyl]silane (EpoPS, 2-(3,4-epoxycyclohexyl)-ethyltrimethoxysilane) and 675 μl of 28% by weight ammonia water were mixed, and reacted at 95° C. for 3 hours. The solution thus obtained (reaction completed solution) was subjected to centrifugal sedimentation by the high-speed centrifugal machine (10,000×g, 5 minutes), pellets thus obtained were washed with 70% ethanol and distilled water repeatedly for several times. Particles subjected to centrifugal sedimentation were stirred by the ultrasonic crushing machine, these silica spheres were observed by the electron microscope, and it was confirmed that particles with average particle diameter of 1160 nm and size control rate of about 10.3% were prepared.

Example 16

Preparation of Silica Particles by TCPS 7.5 μl of 3-thiocyanatopropyltriethoxysilane (TCPS) and 675 μl of 28% by weight ammonia water were mixed and reacted at 99° C. for 3 hours. The solution thus obtained (reaction completed solution) was subjected to centrifugal sedimentation by the high-speed centrifugal machine (10,000×g, 5 minutes), pellets thus obtained were washed with 70% ethanol and distilled water repeatedly for several times. Particles subjected to centrifugal sedimentation were stirred by the ultrasonic crushing machine, these silica spheres were observed by the electron microscope, and it was confirmed that particles were prepared. It was confirmed that particles with average particle diameter of 296 nm and size control rate of 35.1% were prepared.

Example 17

Preparation of Thiol-Containing Particles Derived from AcPS

To 10 μl of 3-acryloxypropyltrimethoxysilane (AcPS) was added 28% by weight ammonia water to give 1 ml, mixed and reacted at 25° C. for 3 days. The solution thus obtained (reaction completed solution) was subjected to centrifugal sedimentation by the high-speed centrifugal machine (10,000×g, 5 minutes), pellets thus obtained were washed with 70% ethanol and distilled water repeatedly for several times. Particles subjected to centrifugal sedimentation were stirred by the ultrasonic crushing machine, these silica spheres were observed by the electron microscope, and it was confirmed that particles with average particle diameter of 540 nm and size control rate of about 18.5% were produced.

Comparative Example 2

Comparative Example—Case where Particle Formation is Attempted in Accordance with Conditions Described in Patent Document 2

According to conditions in method disclosed by Trau et al. shown in Patent Document 2, preparation of new six silica particles which were successfully prepared in the present application was attempted. After acid treatment (100 μl of silica compound (MPS, AcPS or the like), 800 μl of distilled water, 0.1M HCl were mixed and reacted while stirring at 1200 rpm at 25° C.) was carried out for 2 days, base treatment by ammonia was carried out. Samples elapsed 15 minutes, 30 minutes and 8 hours after initiation of the base treatment (to 90 μl of silica solution after acid treatment were mixed 100 μl of distilled water and 0.75 μl of 28% by weight ammonia water and reacted) were observed by the electron microscope.

The following table shows results of preparation of particles of the present invention (MPS, MPES, MPDMS, AcPS, EpoS, and TcPS) attempted under the conditions described in Patent Document 2. Particles formed (O), no particle formed (x), and there are incomplete particles (Δ) are shown. Time in the table shows time elapsed (15 minutes, 30 minutes, 8 hours) after initiation of base treatment which was carried out after acid treatment (2 days).

TABLE 2A

| | Trau's method | | |
|---|---|---|---|
| | 15 min | 30 min | 8 hr |
| MPS | X | Δ | O |
| MPES | X | X | O |
| MPDMS | X | X | X |
| AcPS | X | X | Δ |
| EpoS | X | X | X |
| TcPS | X | X | O |

According to Patent Document 2, time for acid treatment is 1-3 days, and for base treatment, ethanol is added at 5 minutes after or immediately after. It is interpreted that ethanol added was used to stop reaction by base treatment. That is, it is interpreted that according to the method of Patent Document 2, micelle formation and modest particle solidification were performed by acid treatment, and complete particle solidification was performed by base treatment. It is therefore considered that time for base treatment is short, the reason for performing ethanol treatment is to make particle solidification reaction nonuniform, and area where solidification is insufficient becomes pores.

Example 18

Preparation of APS Silica Compound Containing Rhodamine (Labeling Molecule) with Succinimidyl Ester and Preparation of Silica Sphere (Rhodamine-Containing Silica Particles) with the Same (1) As succinimidyl ester compound, Rhodamine Red™* (about 5 mg) was dissolved into 50 μl of DMSO solution, then 3-aminopropyl-triethoxysilane (APS) containing amino group was added to be equimolar to above Rhodamine Red™* C2 maleimide, stirred and reacted with the tube mixer under light shielding for about 2 hours to prepare silica compound containing rhodamine (labeling molecule).

(2) Preparation of label containing silica sphere Next, silica sphere containing rhodamine (labeling molecule) was prepared from silica compound containing rhodamine (labeling molecule). Specifically, 7 μl of reaction solution containing silica compound containing rhodamine (labeling molecule) obtained as described above, 7.5 μl of MPS, and about 675 μl of 27% by weight ammonia water were added, and reacted at 100° C. for about 11 hours. The solution obtained (reaction completed solution) was subjected to centrifugal sedimentation by the high-speed centrifugal machine (10,000×g, 5 minutes), pellets obtained were washed with 70% ethanol and distilled water repeatedly for several times. Particles subjected to centrifugal sedimentation were stirred by the ultrasonic crushing machine, these silica spheres were observed by the fluorescent microscope, and it was confirmed that particles emitted fluorescence of rhodamine.

Example 19

Preparation of APS Silica Compound Containing Rhodamine (Labeling Molecule) with Isothiocyanate (ITC), and Preparation of Silica Sphere (Silica Particle Containing Rhodamine) with the Same (1) Preparation of Silica Compound Containing Rhodamine (Labeling Molecule) with Isothiocyanate As isothiocyanate, Rhodamine Red™* (about 5 mg) was dissolved in 50 μl of DMSO solution, then 3-aminopropyl-triethoxysilane (APS) containing amino group was added to be equimolar to above Rhodamine Red™* C2 maleimide, stirred and reacted with the tube mixer under light shielding for about 2 hours to prepare silica compound containing rhodamine (labeling molecule).

(2) Preparation of Label-Containing Silica Sphere

Next, silica sphere containing rhodamine (labeling molecule) was prepared from rhodamine (labeling molecule) containing silica compound.

Specifically, 7 μl of reaction solution containing silica compound containing rhodamine (labeling molecule) obtained as described above, 7.5 μl of MPS, and about 675 μl of 27% by weight ammonia water were added, and reacted at 100° C. for about 11 hours. The solution obtained (reaction completed solution) was subjected to centrifugal sedimentation by the high-speed centrifugal machine (10,000×g, 5 minutes), pellets obtained were washed with 70% ethanol and distilled water repeatedly for several times. Particles subjected to centrifugal sedimentation were stirred by the ultrasonic crushing machine, these silica spheres were observed by the fluorescent microscope (TE 2000 (with 100-W mercury lamp)) and CCD camera (Digital Sight DS-L1, Nikon)), and it was confirmed that particles emitted fluorescence of rhodamine.

Example 20

Preparation of Silica Particles Containing TAMRA

As follows, (a) silica compound containing 5-carboxytetramethylrhodamine (TAMRA) (labeling molecule) was prepared in advance, and (b) silica spheres containing TAMRA (labeling molecule) were prepared using the silica compound thus obtained.
(a) Preparation of Silica Compound Containing TAMRA (Labeling Molecule)

As succinimidyl ester compound, after 5-carboxytetramethylrhodamine succinimidyl ester (5-TAMRA-SE) (about 1.7 mg) was dissolved in 85 μl of DMSO solution, as silica compound having amino group, 3-(aminopropyl)triethoxysilane (APS) was added to be equimolar to above 5-TAMRA-SE and mixed, stirred and reacted with the tube mixer under light shielding for 2 hours to prepare silica compound containing TAMRA (labeling molecule), and presented to the following (b) preparation of silica spheres.
(b) Preparation of Silica Spheres Containing TAMRA Labeling Molecule To 30 μl of the reaction solution containing silica compound containing TAMRA (labeling molecule) obtained in above (a) were added 30 μl of MPS and about 675 μl of 27% by weight ammonia water, mixed, and reacted at 95° C. for about 10 hours. Subsequently, the reaction completed solution was loaded to high-speed centrifugal machine (10,000× g, 5 minutes), and pellets were collected therefrom. The pellets were washed with 70% ethanol and distilled water alternately. Washing was performed repeatedly by centrifugation for total 6 times. Pellets collected (silica particle) were stirred and dispersed by the ultrasonic crushing machine, then sampled, and observed by fluorescent microscope, and it was confirmed that particles emitted fluorescence of TAMRA. (27-2487-2)

Example 21

Preparation of Silica Particle Containing Alexa Fluor 647

As follows, (a) silica compound containing Alexa Fluor 647 (labeling molecule) was prepared in advance, and (b) silica sphere containing Alexa Fluor 647 (labeling molecule) was prepared using the silica compound thus obtained.
(a) Preparation of Silica Compound Containing Alexa Fluor 647 (Labeling Molecule)

As maleimide compound, Alexa Fluor 647 C2-maleimide (about 1 mg) was dissolved in 50 μl of DMSO solution, and then (3-mercaptopropyl)-trimethoxysilane having thiol group was added to be equimolar to the Alexa Fluor 647 C2-maleimide, mixed, and stirred and reacted with the tube mixer under light shielding for 2 hours to prepare silica compound containing Alexa Fluor 647 (labeling molecule), and presented to the following (b) preparation of silica spheres.
(b) Preparation of Silica Spheres Containing Alexa Fluor 647 Labeling Molecule To 3 μl of the reaction solution containing silica compound containing Alexa Fluor 647 (labeling molecule) obtained in above (a) were added 10 µl of MPS, about 337.5 µl of 2-propanol, and about 337.5 µl of 27% by weight ammonia water, mixed, and reacted at 100° C. for about 2 hours. Subsequently, the reaction completed solution was loaded to high-speed centrifugal machine (10,000×g, 5 minutes), and pellets were collected therefrom. The pellets were washed with 70% ethanol and distilled water alternately. Washing was performed repeatedly by centrifugation for total 6 times. Pellets collected (silica particle) were stirred and dispersed by the ultrasonic crushing machine, then sampled, and observed by fluorescent microscope, and it was confirmed that particles emitted fluorescence of Alexa Fluor 647.
(32-2838-B)

Example 22

Preparation of Silica Particles Containing DY 635

As follows, (a) silica compound containing DY 635 (labeling molecule) was prepared in advance, and (b) silica sphere containing DY 635 (labeling molecule) was prepared using the silica compound thus obtained.
(a) Preparation of Silica Compound Containing DY 635 (Labeling Molecule)
As succinimidyl ester compound, DY 635 N-hydroxysuccinimide ester (about 1 mg) was dissolved in 25 µl of DMSO solution, and then 3-(aminopropyl)triethoxysilane (APS) was added as silica compound having amino group to be equimolar to above DY 635, mixed, and stirred and reacted with the tube mixer under light shielding for 2 hours to prepare silica compound containing DY 635 (labeling molecule), and presented to the following (b) preparation of silica spheres.
(b) Preparation of Silica Spheres Containing DY 635 Labeling Molecule
To 5 µl of the reaction solution containing silica compound containing DY 635 (labeling molecule) obtained in above (a) were added 7.5 µl of MPS and about 675 µl of 27% by weight ammonia water, mixed, and then reacted at 100° C. for about 12 hours. Subsequently, the reaction completed solution was loaded to high-speed centrifugal machine (10,000×g, 5 minutes), and pellets were collected therefrom. The pellets were washed with 70% ethanol and distilled water alternately. Washing was performed repeatedly by centrifugation for total 6 times. Pellets collected (silica particle) were stirred and dispersed by the ultrasonic crushing machine, then sampled, and observed by the fluorescent microscope, and it was confirmed that particles emitted fluorescence of DY 635.
(28-2560-1)

Example 23

Preparation of Silica Particle Containing DY 495

As follows, (a) silica compound containing DY 495 (labeling molecule) was prepared in advance, and (b) silica sphere containing DY 495 (labeling molecule) was prepared using the silica compound thus obtained.
(a) Preparation of Silica Compound Containing DY 495 (Labeling Molecule)
As succinimidyl ester compound, DY 495-X/5-N-hydroxy succinimide ester (about 5 mg) was dissolved in 25 µl of DMSO solution, and then 3-(aminopropyl)triethoxysilane (APS) was added as silica compound having amino group to be equimolar to above DY 495, mixed, and stirred and reacted with the tube mixer under light shielding for 2 hours to prepare silica compound containing DY 495 (labeling molecule), and presented to the following (b) preparation of silica spheres.
(b) Preparation of Silica Spheres Containing DY 495 labeling molecule
To 10 µl of the reaction solution containing silica compound containing DY 495 (labeling molecule) obtained in above (a) were added 10 µl of MPS, and about 675 µl of the mixture of about 337.5 µl of 2-propanol and about 337.5 µl of 27% by weight ammonia water, then mixed, and reacted at 100° C. for about 11 hours. Subsequently, the reaction completed solution was loaded to high-speed centrifugal machine (10,000×g, 5 minutes), and pellets were collected therefrom. The pellets were washed with 70% ethanol and distilled water alternately. Washing was performed repeatedly by centrifugation for total 6 times. Pellets collected (silica particle) were stirred and dispersed by the ultrasonic crushing machine, then sampled, observed by fluorescent microscope, and it was confirmed that particles emitted fluorescence of DY 495.
(29-2576-2)

Example 24

Preparation of Silica Particle Containing DY 505

As follows, (a) silica compound containing DY 505 (labeling molecule) was prepared in advance, and (b) silica sphere containing DY 505 (labeling molecule) was prepared using the silica compound thus obtained.
(a) Preparation of Silica Compound Containing DY 505 (Labeling Molecule)
As succinimidyl ester compound, DY 505X/5-N-hydroxysuccinimide ester (about 5 mg) was dissolved in 25 µl of DMSO solution, and then 3-(aminopropyl)triethoxysilane (APS) was added as silica compound having amino group to be equimolar to above DY 505, mixed, and stirred and reacted with the tube mixer under light shielding for 2 hours to prepare silica compound containing DY 505 (labeling molecule), and presented to the following (b) preparation of silica spheres.
(b) Preparation of Silica Particle Containing DY 505 Labeling Molecule
To 14 µl of the reaction solution containing silica compound containing DY 505 (labeling molecule) obtained in above (a) were added 15 µl of MPS, and about 675 µl of 27% by weight ammonia water, mixed, and then reacted at 95° C. for about 12 hours. Subsequently, the reaction completed solution was loaded to high-speed centrifugal machine (10,000×g, 5 minutes), and pellets were collected therefrom. The pellets were washed with 70% ethanol and distilled water alternately. Washing was performed repeatedly by centrifugation for total 6 times. Pellets collected (silica particle) were stirred and dispersed by the ultrasonic crushing machine, then sampled, and observed by fluorescent microscope, and it was confirmed that particles emitted fluorescence of DY 505.
(27-2488-1)

Example 25

Preparation of Silica Particles Containing Trisdichlororuthenium (II) Hexahydrate As follows, silica spheres containing trisdichlororuthenium (II) hexahydrate (labeling molecule) were prepared by a method for doping the dye to particles.
To 20 µl of 100 mM trisdichlororuthenium (II) hexahydrate reaction solution were added 40 µl of mercaptopropyltriethoxysilane (MPES), about 480 µl of 2-propanol, and about 480 µl of 27% by weight ammonia water, mixed, and reacted at 100° C. for about 3 hours. As comparative example, particles were produced under the same conditions without adding 100 mM trisdichlororuthenium (II) hexahydrate reaction solution. Subsequently, the reaction completed solution was loaded to high-speed centrifugal machine (10,000×g, 5 minutes), and pellets were collected therefrom. The pellets were washed with 70% ethanol and distilled water alternately. Washing was performed repeatedly by centrifugation for total 6 times. Pellets collected (silica particle) were stirred and dispersed by the ultrasonic crushing machine, sampled, and fluorescence (FL2, FL3) was confirmed by flow cytometry. (35-3039-1)

Figure 22:
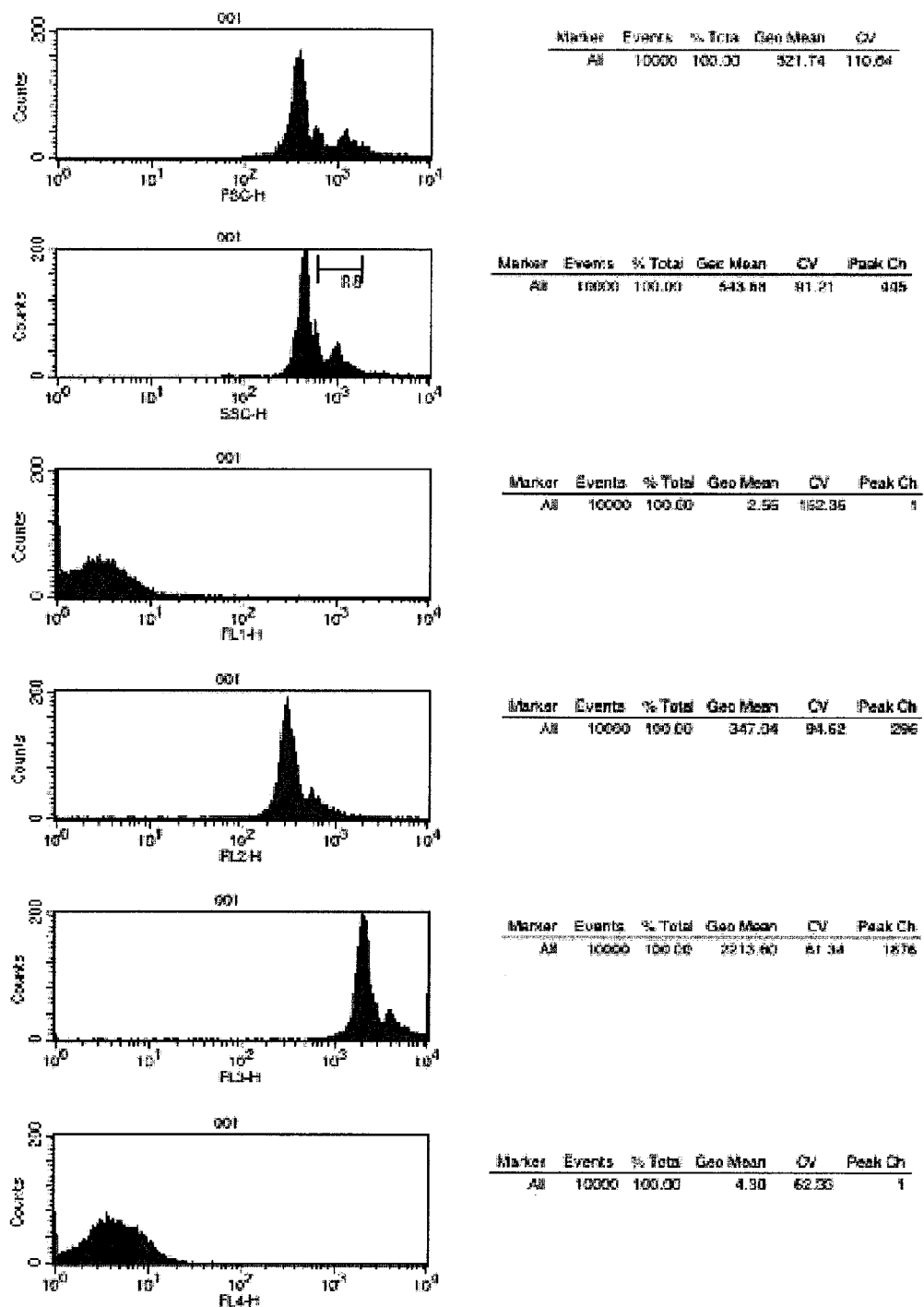
FIG. 22 shows flow cytometry images (with dyes) obtained in Embodiment 25.
Figure 23:
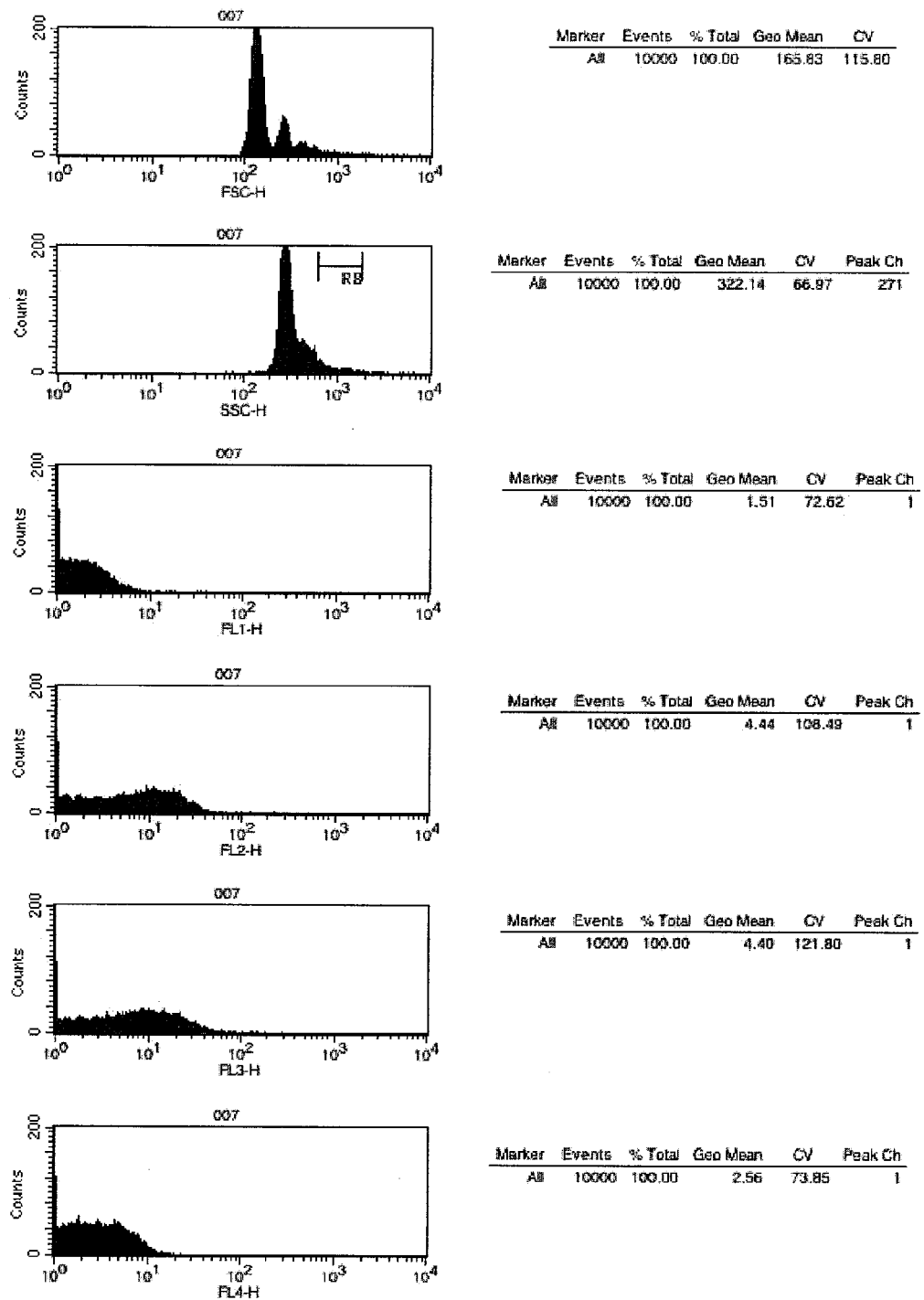
FIG. 23 shows flow cytometry images (without dyes) obtained in Embodiment 25.
Figure 24:
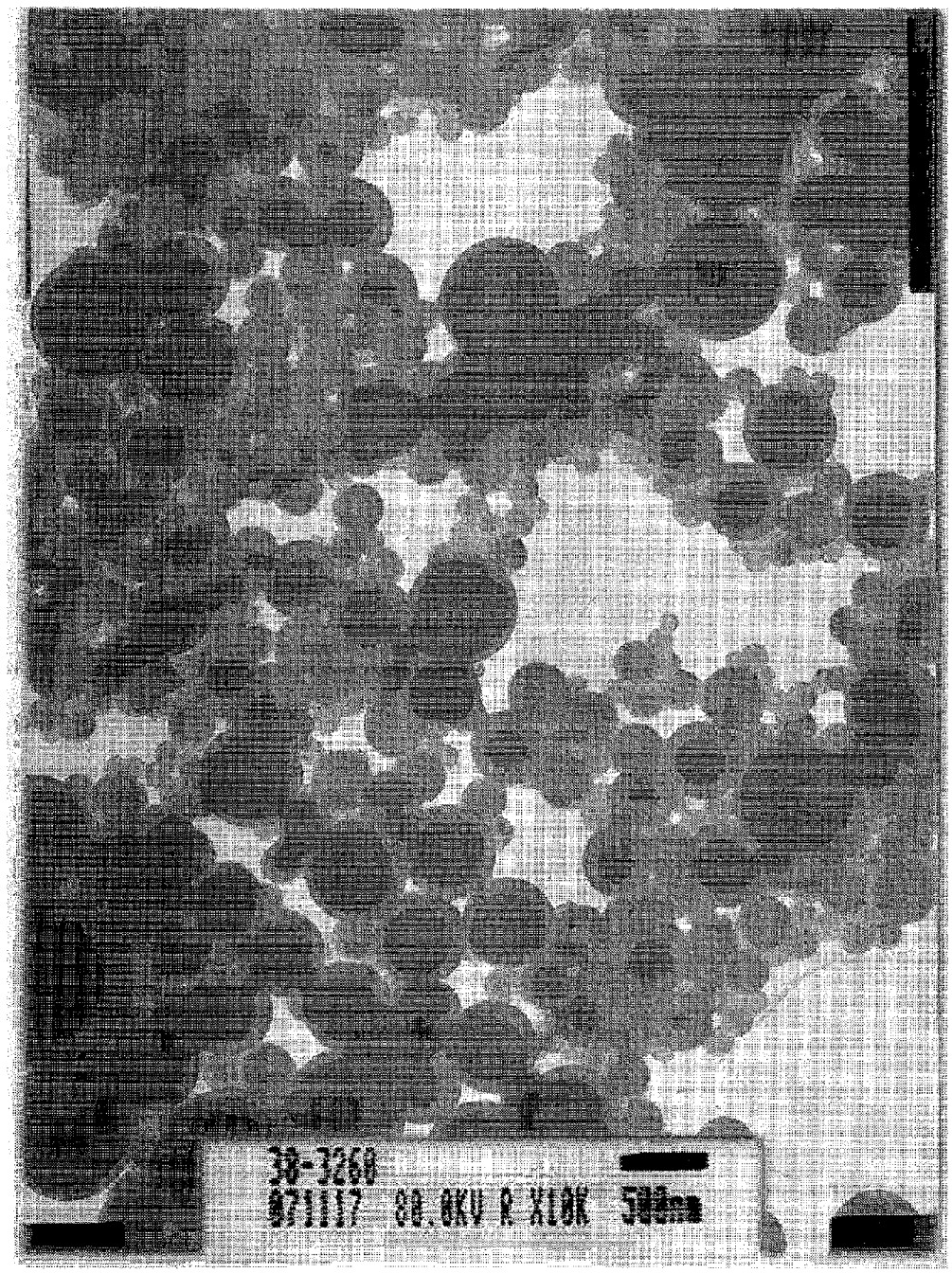
FIG. 24 is an electron microscopic image in Embodiment 28.
Figure 25:
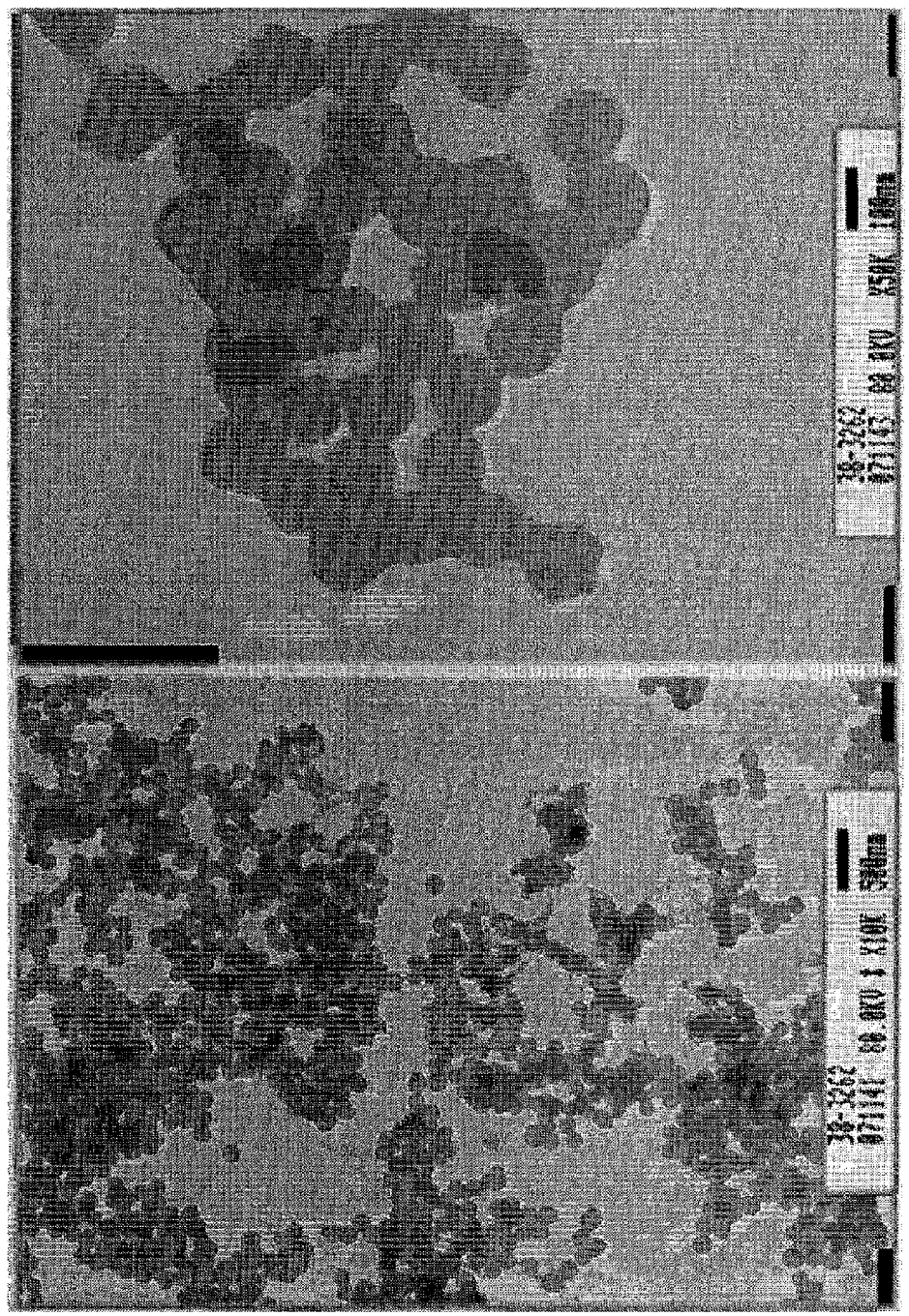
FIG. 25 is an electron microscopic image in Embodiment 29.
Figure 26:
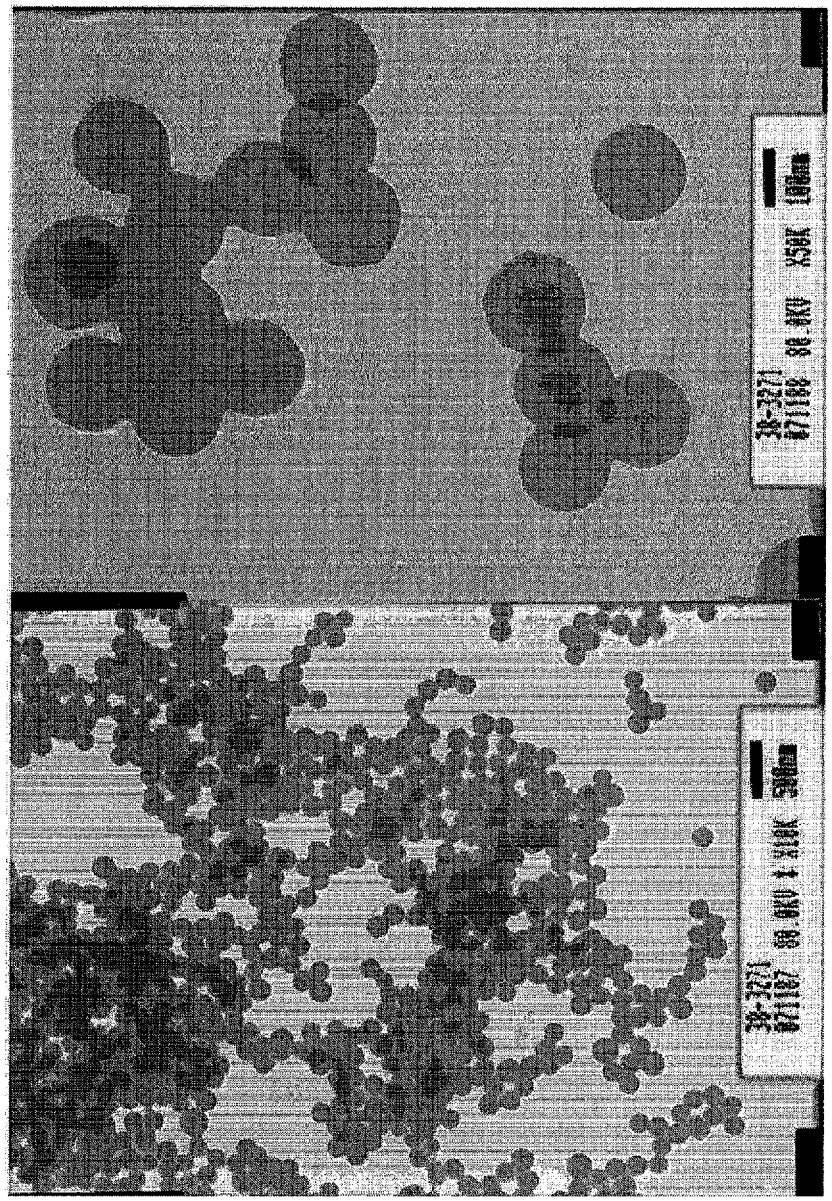
FIG. 26 is an electron microscopic image in Embodiment 30.
Figure 27:
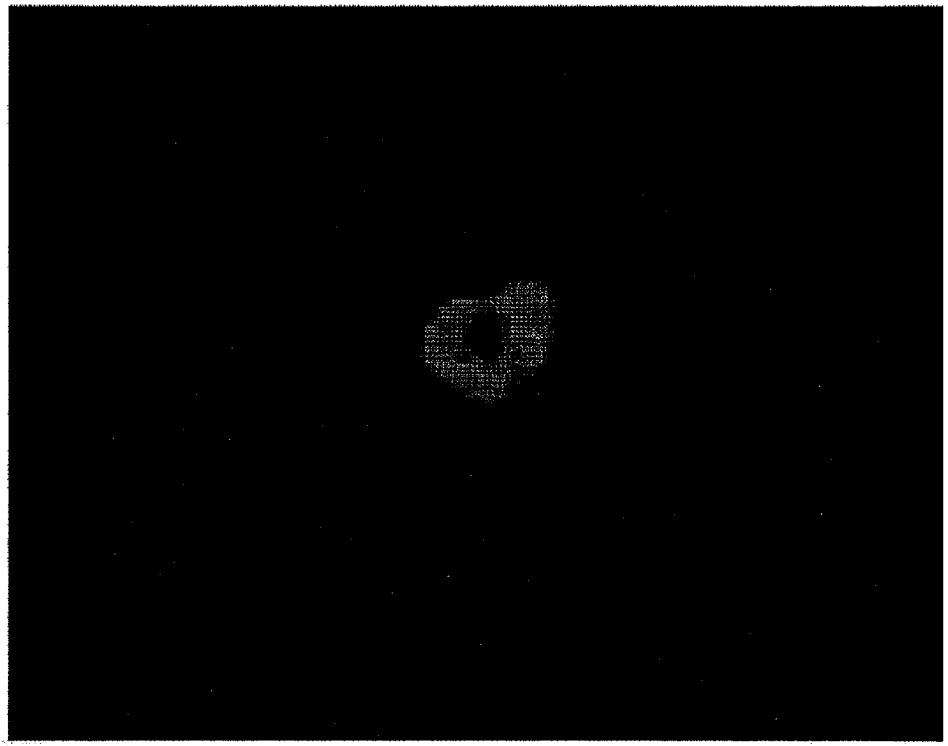
FIG. 27 shows fluorescence microscopic image (a) and electron microscopic image (b) described in Embodiment 31.
Figure 27:
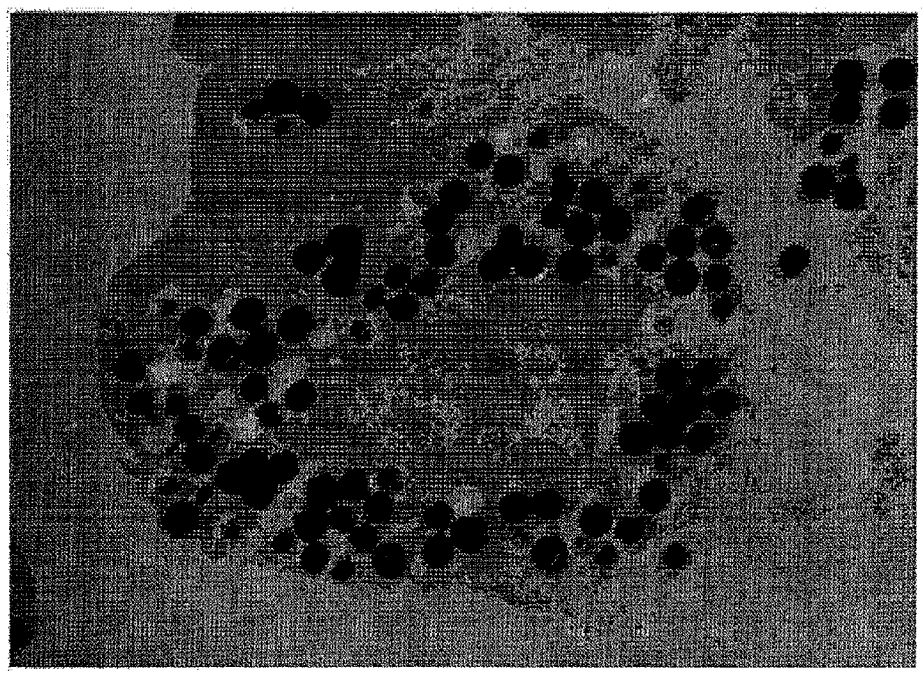

In FIG. 22 and FIG. 23, FIG. 22 shows cases with dye and FIG. 23 shows cases without dye. It can be confirmed in FIG. 22 that peaks move dominantly in FL2 and FL3 by fluorescent emission as compared with FIG. 23. It can be confirmed that dyes are taken into particles favorably, thereby emitting fluorescence.

Comparative Example 3

Forming Rate of MPS NP

Forming rate of MPS NP was compared with forming rate of TEOS NP under the same conditions with transmission electron microscope (TEM).

To 68 μl of water were added 325 μl of ethanol, 21 μl of TEOS or 19 μl of MPS, and 36 μl of 27% by weight ammonia water, mixed, and reacted at room temperature.

The experimental conditions are used in ordinary Stober method, and with this method, it can be confirmed that particle formation of MPS are slower than TEOS. Further, with MPS, the solution becomes clouded in several hours and does not result in particle formation. That is, with conventional method, it looks as if production of MPS particles is not possible. However, as found by the present inventors, it has been demonstrated that particle could be produced within extremely short time by reaction of MPS under conditions, which are not used in ordinary methods, i.e., high-temperature and/or high-ammonia conditions.

(Reaction without Using Conditions by Conventional Stober Method—without Using High-Temperature/High-Ammonia Conditions)

Figure 9:
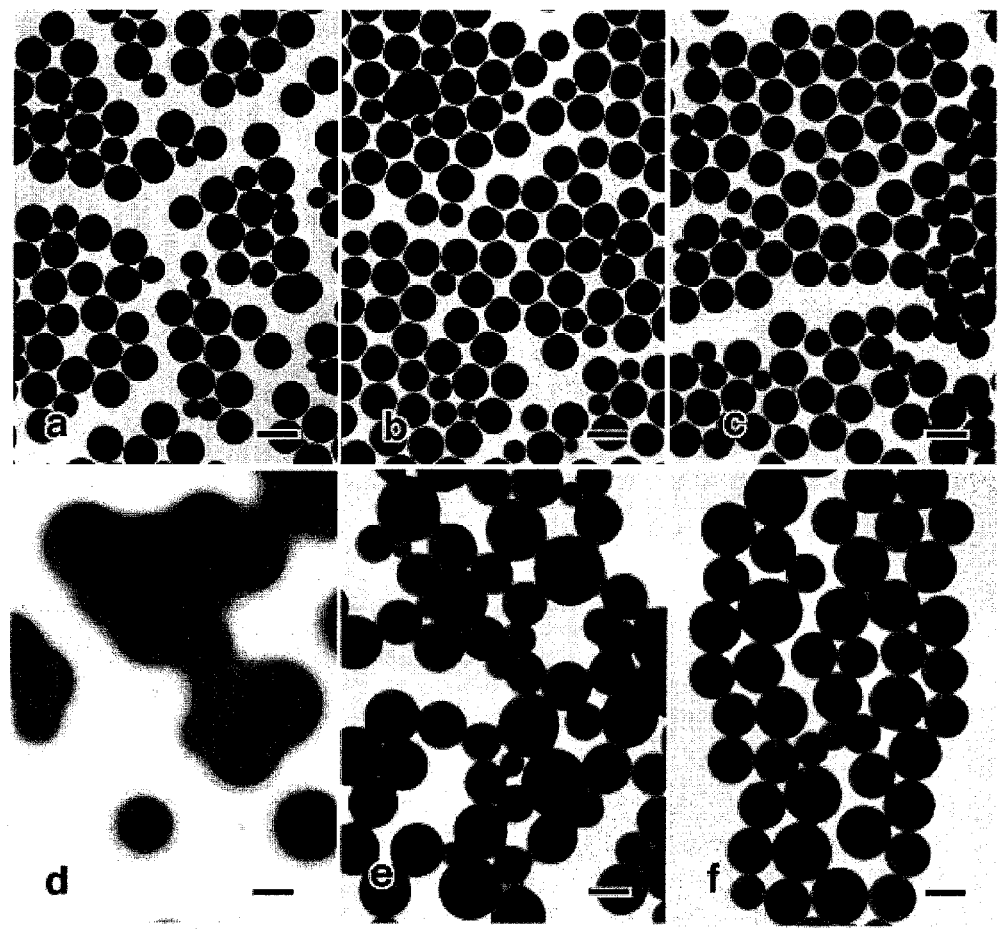
FIG. 9 shows transmission electron microscopic image of fluorescent nano silica particles as time function. TEOS NP (a to c) and MPS NP (d to f) were observed 9 hours later (a, d), 1 day later (b, e) and 2 days later (c, f). The scale bar is equivalent to 500 nm.

TEOS NP could be observed clearly at 9 hours after initiation of reaction (FIG. 9a-FIG. 9c). In the research result by this TEM, TEOS NP did not change significantly after one day elapsed and before 2nd day. Therefore, it is judged that TEOS NP is formed thoroughly within the first 9 hours of the reaction time. Contrary to this, formation of MPS particles proceeds in different fashion. Interface portion of the products is indistinct after 9 hours elapsed, some are fused each other, and others are separated (FIG. 9d). Subsequently, the products were washed with 70% ethyl alcohol/water and then loaded to the centrifugal machine (10,000×g 5 minutes), and nano particles were not collected. Two days later, definite MPS NP was observed (FIG. 9e and FIG. 9f). These results suggest that formation of MPS NP takes place slower than TEOS NP under the same conditions.

It is considered that particle growth process for MPS is different from particle growth process for TEOS. Formation of TEOS NP by Stober method is started by hydrolysis of silica precursor by ammonium hydroxide, then self-polymerization, formation of silica matrix, and sedimentation of TEOS NP follow. Detailed mechanism of formation of MPS NP has not been identified yet. Although MPS reaction mixture became clouded in several hours, MPS particles were not recovered after washing step. Another process is assumed that first, MPS micelle is formed, and then hydrolysis and polymerization of MPS due to ammonium hydroxide occur in the micelle, thereby forming nano particles. When compared with TEOS nano particles, MPS nano particles exhibit a broad size distribution depending on concentration of MPS in the reaction mixture. That is, size distribution of TEOS NP is different from that of MPS NP.

For example, on the second day, size of TEOS NP is in a range of 250 nm-570 nm (FIG. 9c), while size of MPS NP is in a range of 350 nm-1200 nm (FIG. 9f). MPS NP having narrow size distribution is needed for a certain application, and the present inventors have studied methods for preparing such MPS NP. It is considered that MPS is capable of producing dipodal alkoxysilane by formation of disulfide binding between thiol residues of MPS, and alkoxysilane obtained can produce POM nano particles.

(Experimental Conditions of the Present Invention—Use of High-Temperature Conditions and High-Ammonium Conditions)

The present inventors synthesized MPS NP and TEOS NP containing fluorescence dye as follows.

To 10 mM MPS was mixed equal amount of 10 mM Rhodamine Red C2 maleimide, reacted for 2 hours to prepare MPS-rhodamine. To 68 μl of water were added 325 μl of ethanol, 21 μl of TEOS or 19 μl of MPS, and 36 μl of 10 mM MPS-rhodamine and 27% by weight ammonia water, mixed, and reacted at room temperature for 2 days. The solution obtained (reaction completed solution) was subjected to centrifugal sedimentation by the centrifugal machine (10,000×g, 5 minutes), and pellets obtained were washed with 70% ethanol and distilled water several times. Particles subjected to centrifugal sedimentation were stirred by the ultrasonic crushing machine.

In the present study, the present inventors characterized these particles and compared with quantum dot.

(Table 3 Comparison of fluorescence intensity between fluorescent nano silica particles and quantum dot)

TABLE 3

|  | MPS-NPs-R | TEOS NPs-R | Q-dot 605 | Q-dot 605 |
| --- | --- | --- | --- | --- |
| Concentration | 0.10 mg/mL | 0.11 mg/mL | 40 nM | 40 nM |
| Diameter (mean) (nm) | 490 | 200 | 20 | 20 |
| Number of particles (number/mL)$^a$ | $7.1 \times 10^9$ | $2.0 \times 10^9$ | $2.4 \times 10^{13}$ | $2.4 \times 10^{13}$ |
| Measured λ (Ex/Em)$^a$ (nm) | 570/590 | 570/590 | 570/590 | 350/605 |
| Intensity | 14.7 | 13.7 | 17.3 | 505.4 |
| Intensity/Particle$^c$ | $6.8 \times 10^{-8}$ | $6.9 \times 10^{-9}$ | $7.2 \times 10^{-13}$ | $2.1 \times 10^{-11}$ |
| Ratio | 1 | 0.1 | $1.1 \times 10^{-5}$ | $3.1 \times 10^{-4}$ |
| Specific intensity$^c$ | $1.5 \times 10^2$ | $1.2 \times 10^2$ | $2.2 \times 10^2$ | $6.3 \times 10^2$ |
| Ratio | 1 | 0.8 | 0.15 | 4.2 |

$^a$Weight per one particle was calculated using $4\pi \times ((Diameter/2)^3/3) (mm^3) \times 2.3$ (specific gravity). It was assumed to divide concentration by weight per particle, and the number of fluorescent nano silica particles was calculated.
$^b$Intensity was divided by the number of particles.
$^c$Intensity was divided by the number of particles and further divided by cubic volume of one particle.

Fluorescence intensity of quantum dot Q-dot 605 was assessed under the following two conditions. The first conditions are same as the conditions for assessment of fluorescence intensity of fluorescent nano silica particles containing rhodamine red. In particular, excitation wavelength and luminescence wavelength are 570 nm and 590 nm, respectively. The second conditions are optimum conditions for Q-dot 605. In particular, excitation wavelength and luminescence wavelength are 350 nm and 605 nm, respectively. As summarized in Table 3, fluorescence intensity of MPS NP containing rhodamine is higher than fluorescence intensity of quantum dot. This is considered to be attributable to when the size of nano silica particles is greater and the amount of dyes incorporated is large. Next, specific fluorescence intensity was calculated by dividing total fluorescence intensity by cubic volume of particles (see Table 3). Specific fluorescence intensities of MPS nano particles measured at excitation at 570 nm and luminescence at 590 nm were 7 times and one fourth of specific fluorescence intensities of quantum dot measured at excitation at 350 nm and luminescence at 605 nm, respectively.

Figure 10:
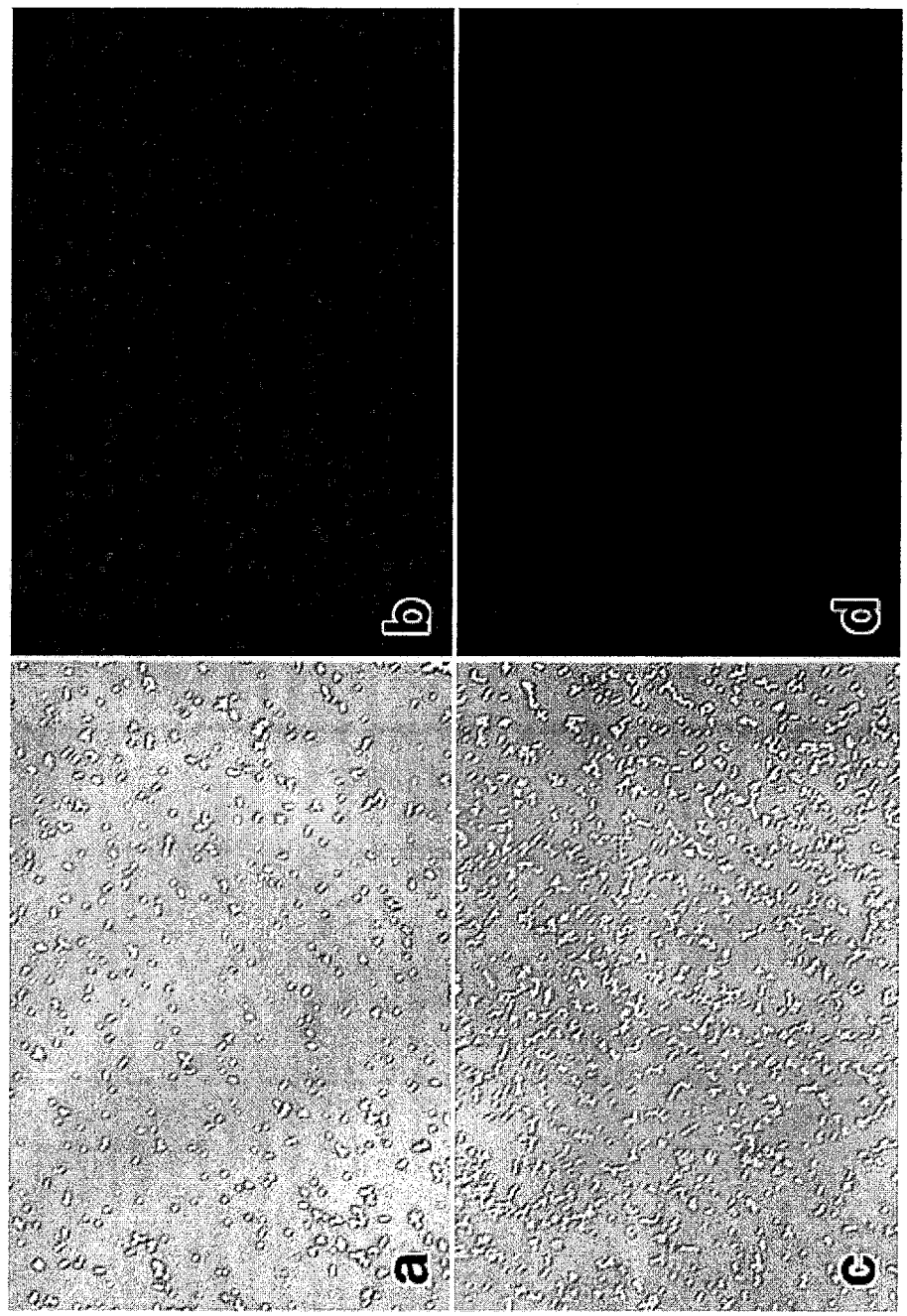
FIG. 10 shows fluorescence microscopic images of nano silica particles having maleimide rhodamine conjugate on the surface layer. MPS NP (a, b) and TEOS NP (c, d) altered by maleimide rhodamine red conjugate on the surface layer were observed under bright field (a, c) and 540/12 nm excitation state (b, d).
Figure 11:
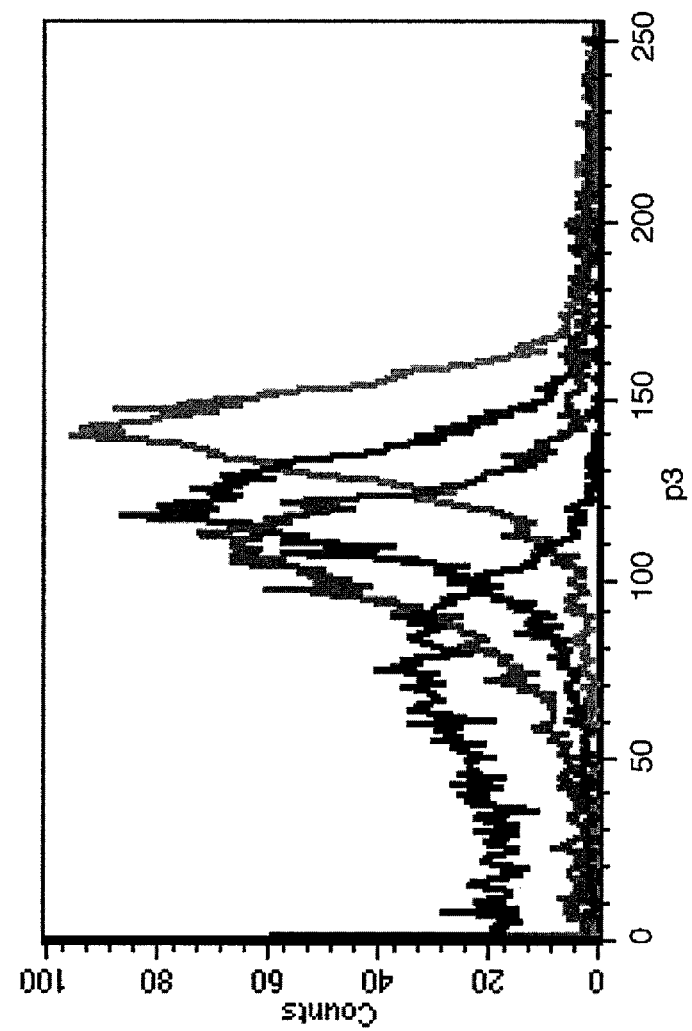
FIG. 11 shows flow cytometry analysis of surface layer fluorescent regulated MPS NP. MPS NP altered on the surface layer by maleimide rhodamine red at various concentrations were analyzed under the same conditions.
Figure 12:
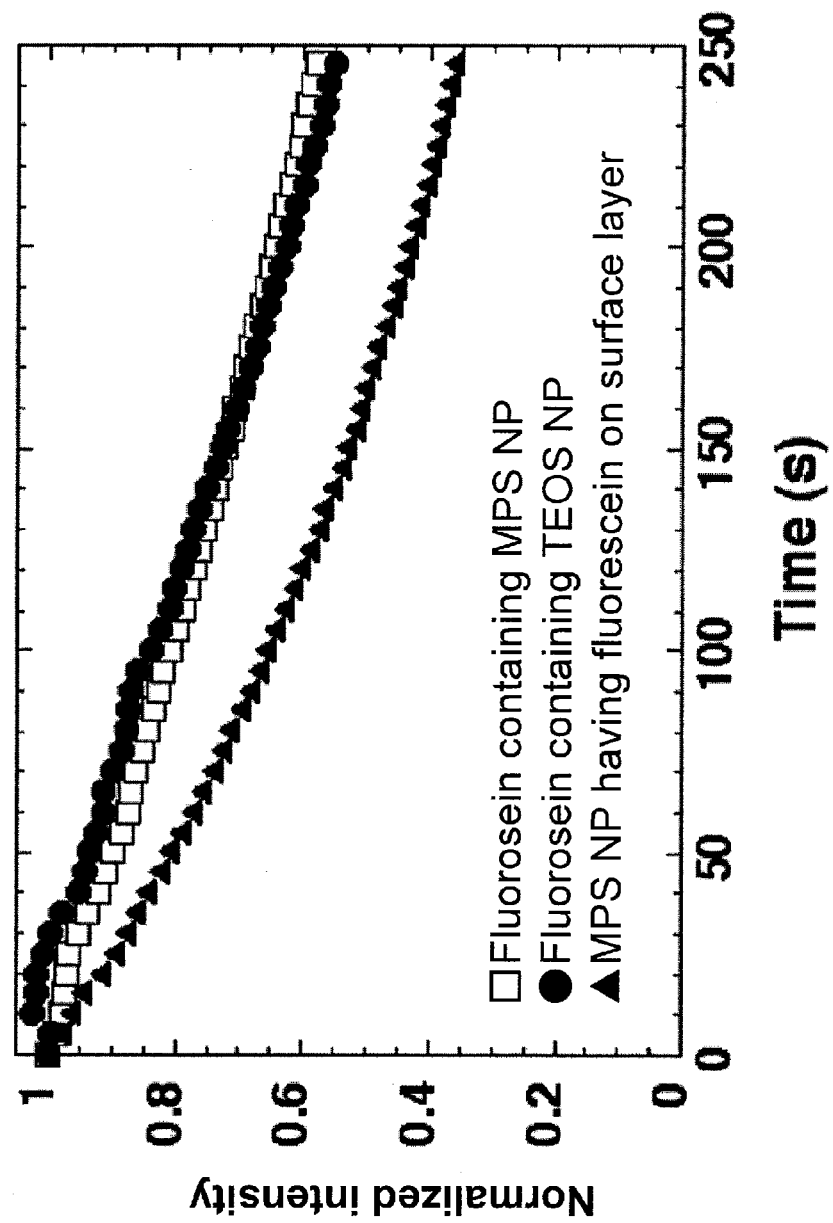
FIG. 12 shows comparison of photostability between TEOS NP (white square) and MPS NP (black circle) by fluorescence microscope. Both NPs include fluorescent dye, while MPS NP means one altered on the surface layer by rhodamine red (black triangle).

In the studies by the present inventors performed thus far, TEOS NP containing fluorescence dye was prepared using the same method and compared with Q dot 525. Specific intensity of TEOS NP containing fluorescence dye is one third of the quantum dot thereof under the same conditions, and $1/48$ of specific fluorescence intensity of quantum dot under the optimum conditions. In the case of silica nano particles containing rhodamine red, relative intensity with regard to quantum dot was improved as compared with nano silica particles containing fluorescence dye. These results suggest that improvement of the fluorescence intensity is possible by selecting appropriate dyes to be incorporated in the silica network. Since specific intensities of TEOS and MPS NP are similar, efficiency for incorporating rhodamine dye into their silica network does not differ significantly between the two. Further, as shown in the report of TEOS NP, fluorescent MPS NP can be prepared as a plurality of nano silica particles containing fluorescence regulated nano silica particles and two types of fluorescence dyes. Fluorescent nano particles containing MPS NP and TEOS NP have high fluorescence intensity, and fluorescence intensity of nano silica particles can be increased as compared with fluorescence intensity of quantum dot by improving synthesis method and selection method of fluorescence dyes. MPS NP has another advantage in addition to that of conventional TEOS NP. That is, the surface layer of MPS NP can be altered with ease. This reactivity of MPS NP is a consequence of existence of thiol residue on its surface layer and this existence allows, for example, alteration thereof by the use of maleimide conjugated fluorescence dye. MPS NP was characterized by reaction with dye conjugated with maleimide and using fluorescent microscope and flow cytometry, and comparison was made with those of TEOS NP. MPS NP was reacted with rhodamine red conjugated with maleimide, and then, particles obtained emitted fluorescence. After the reaction, washing and centrifugation were performed, and then, pellets of MPS NP changed from white to red color. MPS NP revealed bright and definite fluorescent emission under the fluorescent microscope (FIG. 10a and FIG. 10b). As control experiment, TEOS NP was also reacted with rhodamine red-maleimide conjugate. Although TEOS NP pellets were white after washing, observation by the fluorescent microscope revealed that no fluorescence was emitted from this NP even under the same conditions of MPS NP (FIG. 10c and FIG. 10d). These findings show that surface layer binding with rhodamine red maleimide conjugate is specific for MPS NP, which indicates that MPS NP presents many thiol residues reactive with the dye. Next, in order to assess fluorescence intensity, MPS NP with fluorescein bound onto the surface layer was investigated using flow cytometry. MPS NP (average diameter about 450 nm; particle diameter distributes from 200-600 nm) was reacted with fluorescein-maleimide conjugate at various concentration and analyzed by flow cytometry. The MPS NP emitted fluorescence at various intensities (FIG. 11). According to these results, it is shown by analysis using flow cytometry that efficiency of binding of fluorescence dye on MPS NP via thiol residue is good, while the fluorescence intensity is adjustable. The present inventors showed that, after surface layer alteration by the fluorescence dye, MPS NP could be utilized for flow cytometry analysis and microscopic observation. Using fluorescent microscope, the present inventors made comparison of the photostability between TEOS NP in which rhodamine red is incorporated into particles, TEOS NP, and MPS NP with rhodamine bound onto surface layer thereof. Curves representing normalized fluorescence intensity of single particle of TEOS NP and MPS NP having rhodamine in particles thereof show favorable photostability, both still hold more than about 500 of the initial value at 250 seconds after continuous luminescence, and stabilities of the both were nearly identical (FIG. 12). Photostability of MPS NP having rhodamine on the surface layer was about 40% at 250 seconds thereafter. The initial values, i.e., values at elapsed time zero, of TEOS NP containing rhodamine red, MPS NP containing rhodamine red, and MPS NP having rhodamine red on the surface layer were 175,889 a.u., 120,582 a.u., and 403,338 a.u., respectively, and the same at 250 seconds later was 111,351 a.u., 66,549 a.u., and 147,294 a.u., respectively. Their fluorescence could be confirmed with the naked eye. Fluorescence intensity of MPS NP with altered surface layer was the highest among all NP tested, while photostability was not necessarily better than others. In the case of MPS NP having rhodamine red on the surface layer, many fluorescence dyes were bound to surface layer thereof, while the surface layer was exposed to solvent and oxygen which the solvent had. Contrary, in NP containing fluorescent dye, since the dye is isolated somewhat from external environments by particles thereof, rate of exposure to oxygen molecules is low. This difference can well explain differences observed for photostability. Zeta potential analysis of TEOS NP and MPS NP was performed for characterization of surface layer charge of NP and confirmation of surface layer functionalization.

TABLE 4

(Zeta potential of nano silica particle)

| (Nano particle) | (Zeta potential) |
| --- | --- |
| TEOS NP | −38.7 |
| TEOS NP containing rhodamine red | −36.0 |
| MPS NP | −52.2 |
| MPS NP containing rhodamine red | −52.1 |
| MPS NP presenting rhodamine red surface layer | −32.2 |
| MPS NP presenting NeutrAvidin surface layer | −19.2 |

As shown in Table 4, zeta potential of MPS NP is far more negative than zeta potential of TEOS NP. It is considered that a difference of zeta potential is caused due to that OH-group is present on the surface for TEOS particle and SH-group is present on the surface in addition to OH-group for MPS particle. As for the structure, it is understood that in MPS particles, many SH-groups are present on the surface as compared with TEOS particle. Zeta potentials of MPS NP and TEOS NP containing rhodamine red therein were not significantly different from zeta potential for the case without dye, respectively. Meanwhile, zeta potential of MPS NP with the surface layer treated by rhodamine red-maleimide conjugate or NeutrAvidin-maleimide conjugate decreased substantially. These results show that NP with rhodamine red incorporated in particles does not show existence of fluorescent dye on the surface layer and as a result, zeta potential is not influenced. As discussed hereinafter in the present specification, conjugation of protein to surface layer of MPS NP via thiol-maleimide reaction is efficient and can alter zeta potential of NP significantly. Since thiol residue is present on the surface layer as prepared without additional procedures, it can be said that MPS NP is a special existence. These are negative throughout in zeta potential as compared with TEOS NP.

(Surface Layer Alteration Characteristics of MPS NP)

Figure 13:
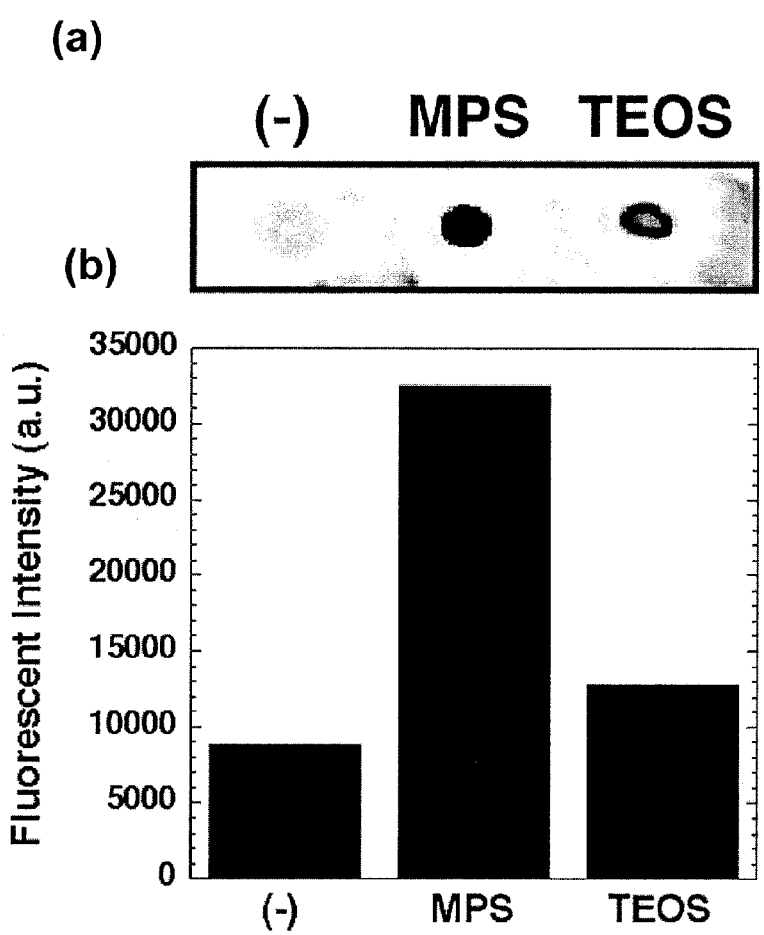
FIG. 13 shows dot-blot analysis of binding ability of silica particles to protein. Nano particles dot-processed on a glass slide were reacted with Cy3 conjugated anti-goat IgG, analyzed by fluorescence image analytical instrument (a), and intensities were plotted (b).
Figure 14:
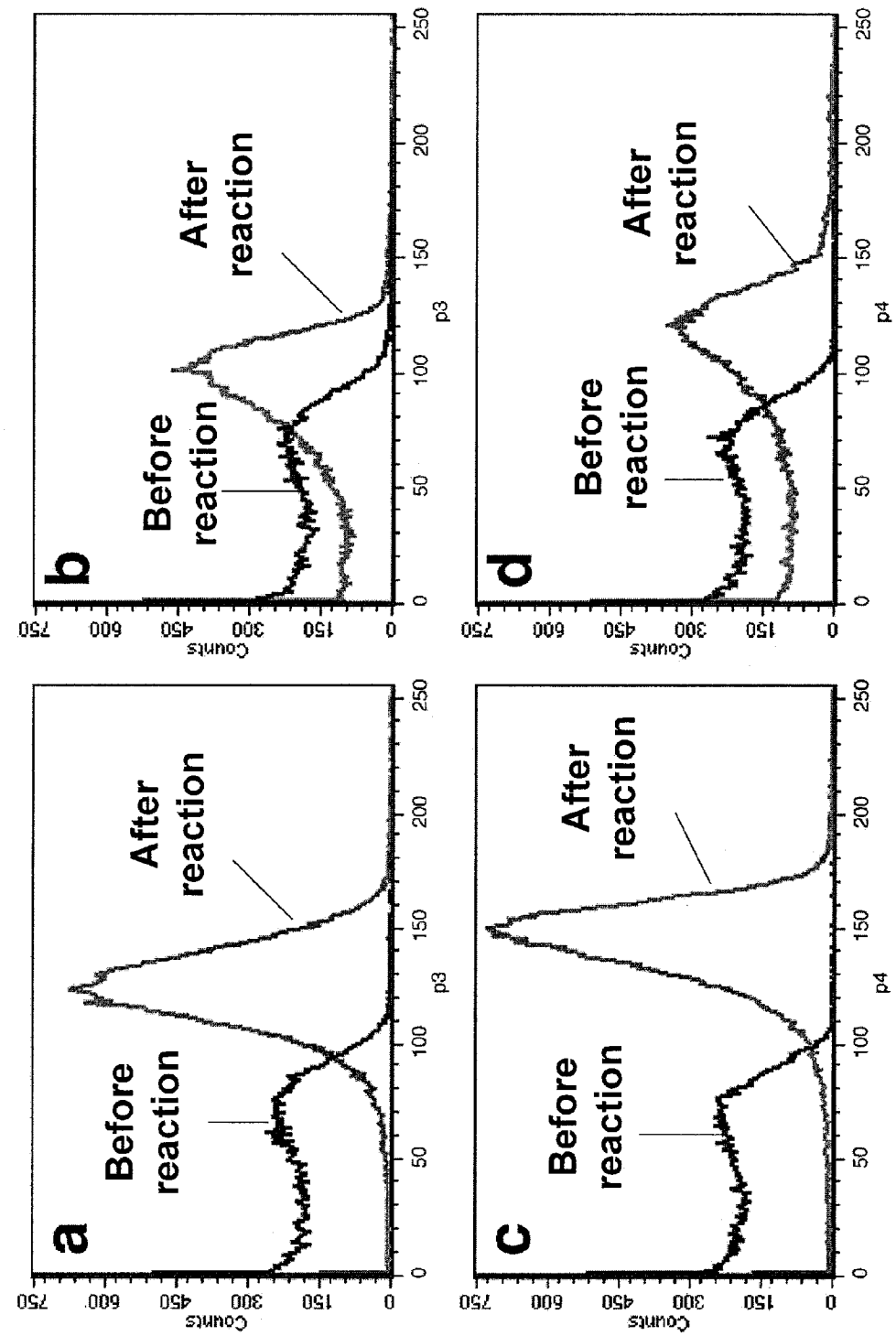
FIG. 14 shows flow cytometry analysis of nano silica particles altered on the surface layer by protein. MPS NP (a, c) and TEOS NP (b, d) were altered by GFP (a, b) or phycoerythrin conjugated streptavidin (PCS) (c, d), and the resultants were analyzed.
Figure 15:
FIG. 15 shows fluorescence microscopic image of MPS NP altered by GFP. MPS NP altered by GFP could be detected by fluorescence microscope. These particles were fluorescent and dispersant.

The present inventors investigated surface layer alteration characteristics of MPS NP by use of flow cytometry, fluorescence image analysis, and fluorescent microscope. The present inventors performed dot blotting by using these NP for comparison of simplicity between MPS NP surface layer and TEOS NP surface layer. Each of equal amounts of NP was dropped onto a glass slide and dried, then reacted with the solution containing Cy3 conjugated anti-goat IgG and investigated with fluorescence image analyzer. MPS NP spot showed that intensity resulting from Cy3 conjugated anti-goat IgG is markedly higher than the spot of TEOS NP (FIG. 13a). Fluorescence intensity of the MPS was about 3-folds of that of TEOS NP (FIG. 13b). These results showed that MPS NP on the slide glass could adsorb larger amount of proteins than TEOS NP. Further, the glass slide with altered MPS NP showed significant improvement of protein adsorption, which then indicated that MPS NP is useful for chip base technology. Next, the present inventors compared surface layer characteristics of MPS NP and TEOS NP in the solution. The NP solution was mixed with protein solution containing either green fluorescent protein (GFP) or phycoerythrin conjugated streptavidin. After mixed with GFP or phycoerythrin conjugated streptavidin, flow cytometry peak relating to MPS NP shifted remarkably to the right due to fluorescence from GFP as compared with TEOS NP (FIG. 14). These findings showed that MPS NP adsorbed proteins more efficiently in the solution as compared with TEOS NP. Observation by the microscope was performed to assess dispersion of MPS NP altered by the protein on the surface layer. The MPS NP solution mixed with the solution containing GFP shows that NP is dispersed favorably by indicating definite fluorescence (FIG. 14). According to these findings, comparison with TEOS NP reveals that MPS NP can be altered very efficiently by GFP while it holds more favorable dispersibility than TEOS NP. MPS NP altered by GFP could be detected and observed by flow cytometry and fluorescent microscope. Potential usability of MPS NP is highly expected in biological studies including beads assay in which flow cytometry using MPS NP is employed.

Alteration of TEOS by silylation treatment of nano silica particles with 3-mercaptopropyl-trimethoxysilane or N1-[3-(trimethoxysilyl-propyl]diethylene triamine was already reported. The silylation treated silane NP was conjugated with oligonucleotide being disulfide altered via thiol/disulfide exchange reaction and conjugated with enzyme and antibody by cross-linking with amine by use of glutaraldehyde. Further, recently, nano silica particles were prepared and surface layer was altered via co-hydrolysis by using TEOS and various organic silane reagents. This method could reduce agglomeration of amino-altered NP. In the present study, MPS NP was synthesized via one-stage synthesis (one-pot synthesis) and thiol residue was synthesized on the surface layer thereof without other additional procedures. This MPS NP showed extremely good dispersion as compared with TEOS NP and larger absolute value of zeta potential in negative value. MPS NP gives assurance for various biological applications for possibility relating to surface layer alteration, and its aspects including bioassay and drug delivery system are worthwhile for further investigations in regard to availability thereof. Thiol residue on NP has various advantages for alteration and functionalization of nano particles. Thiol residue can be reacted with various chemical coupling agents (e.g., alkyl halide and maleimide). The thiol group can easily form covalent binding with other molecule. In recent years, various maleimide conjugated molecules (fluorescent dye, streptavidin, polyethylene glycol and others are mentioned) are available on the market. As described in the present specification, reaction conditions are simple and conjugation efficiency is extremely high. Further, thiol/disulfide exchange reaction is useful for conjugation of thiol residue between oligonucleotide and nano silica particles, and is also useful for conjugation of thiol residue between a certain protein and another protein. In the present specification, the present inventors has demonstrated a method further preferable for production of MPS NP which can be utilized in various applications.

Example 26

Application to Beads Assay

For MPS silica particles of the present invention, primary reaction detection in which the particle is directly reacted with fluorescently-labeled protein to be bound on the particle and is assessed by flow cytometry, and secondary reaction detection in which antigen solution is reacted to be bound on the particle, washed, and reacted with fluorescently-labeled antibody, were performed.

Specific procedures of the assay are as follows:
(A) Thiol silica particle to be used (MPS, MPES, MPDMS) were synthesized as described in Example 2 or Example 5.
(B) MPS silica particles synthesized were directly reacted with fluorescently-labeled protein.

Detailed experimental conditions and results are as follows:

Experiment 1

FITC labeled anti-sheep antibody IgG solutions at various concentrations (39.1-10,000 ng/ml) were prepared. 5 µl of FITC labeled anti-sheep antibody IgG solution with each concentration and 5 µl of particle solution were added to a test tube for flow cytometry, mixed well, diluted with 490 µl of distilled water (without allowing time especially for reaction), and measured by the flow cytometry.

Figure 16:
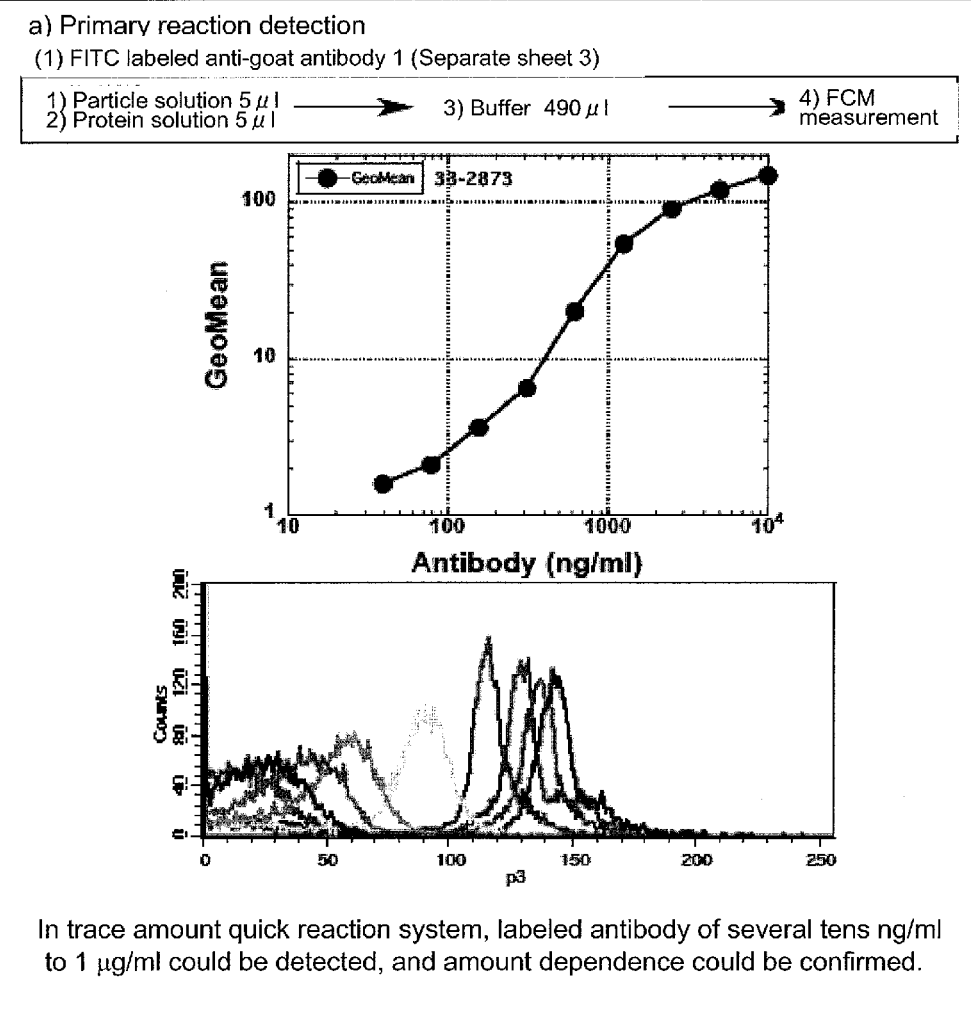
FIG. 16 shows that FITC labeled anti-sheep antibody IgG solution binds to particles in concentration dependent fashion in short time, upper graph shows correlation between concentration of FITC labeled anti-sheep antibody IgG solution and fluorescence intensity detected by binding thereof, while vertical axis represents fluorescence intensity and horizontal axis represents concentration of FITC labeled anti-sheep antibody IgG solution. Lower graph is a chart which shows that each peak varies in concentration dependent fashion by antibody concentration. Measurements could be made quickly in concentration dependent fashion from several tens ng/ml to several μg/ml for a slight amount of sample (measurement target solution: 5 μl).

FIG. 16 shows that FITC labeled anti-sheep antibody IgG solution binds to particles in concentration dependent fashion in short time, upper graph shows correlation between concentration of FITC labeled anti-sheep antibody IgG solution and fluorescence intensity detected by binding thereof, while vertical axis represents fluorescence intensity and horizontal axis represents concentration of FITC labeled anti-sheep antibody IgG solution. Lower graph is a chart which shows that each peak varies in concentration dependent fashion by antibody concentration. Measurements could be made quickly from several tens ng/ml to several µg/ml for a sample as trace amount as 5 µl. (Graph at upper part in FIG. 16 shows plotting of the results shown in the following table and findings by the flow cytometry are shown at lower part. 10000 ng/ml is corresponding to blue color at the rightmost in the lower figure.)

| Ab (ng/ml) | GeoMean |
|---|---|
| 39.0625 | 1.59 |
| 78.125 | 2.09 |
| 156.25 | 3.59 |
| 312.5 | 6.43 |
| 625 | 20.48 |
| 1250 | 54.32 |
| 2500 | 90.31 |
| 5000 | 119.38 |
| 10000 | 147.3 |

Experiment 2

FITC labeled anti-sheep antibody IgG solutions at various concentrations (0.01-100 ng/ml) were prepared. 600 μl of FITC labeled anti-sheep antibody IgG solutions at various concentrations and 5 μl of particle solution were added to the test tube for flow cytometry, mixed well, reacted for 10 minutes, and then measured by the flow cytometry.

Figure 17:
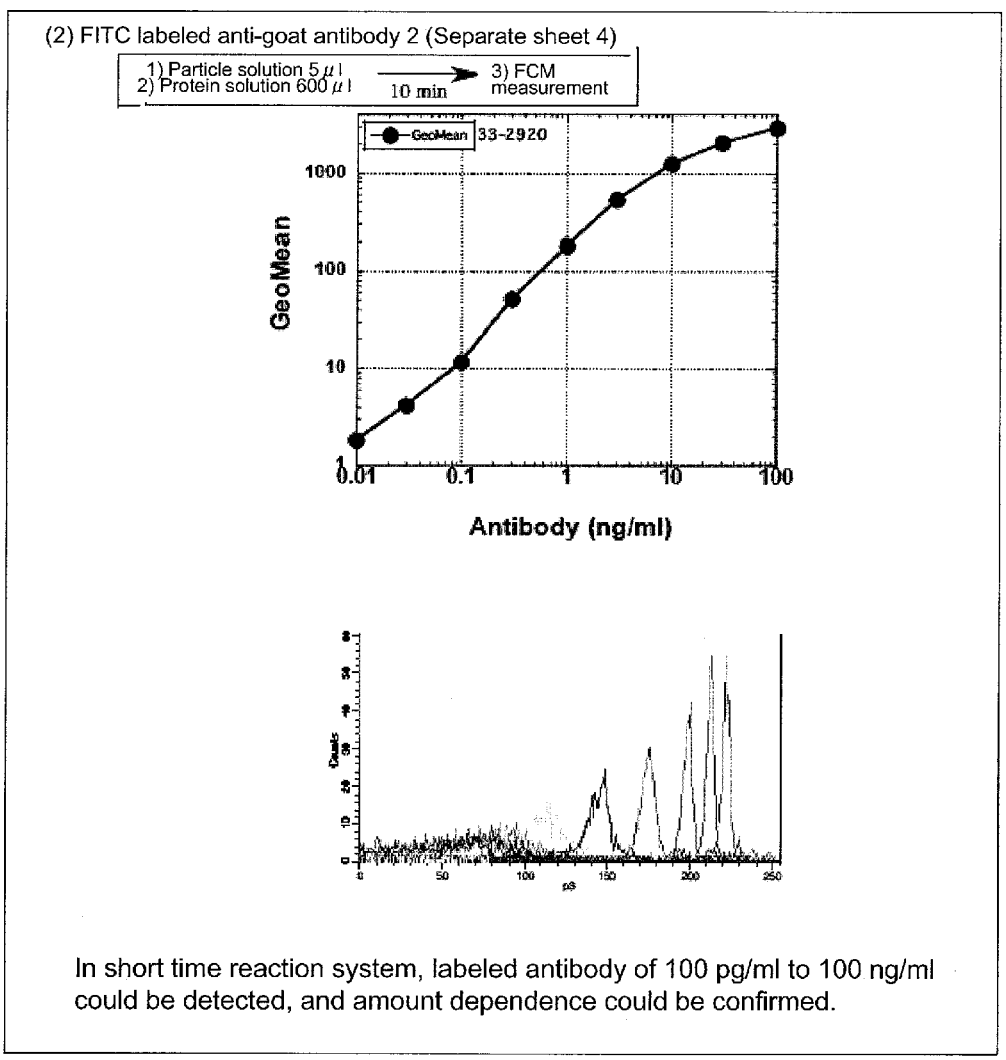
FIG. 17 shows that FITC labeled anti-sheep antibody IgG solution binds to particles in concentration dependent fashion and that, in particular, detection of binding thereof is possible even at concentration not more than ng/ml concentration, upper graph shows correlation between concentration of FITC labeled anti-sheep antibody IgG solution and fluorescence intensity detected from particles by binding thereof, vertical axis represents fluorescence intensity and horizontal axis represents concentration of FITC labeled anti-sheep antibody IgG solution. Lower graph is a chart which shows that each peak varies in concentration dependent fashion by antibody concentration.

FIG. 17 shows that FITC labeled anti-sheep antibody IgG solution binds to particles in concentration dependent fashion and that, in particular, detection of binding thereof is possible even at concentration less than ng/ml, upper graph shows correlation between FITC labeled anti-sheep antibody IgG solution concentration and fluorescence intensity detected from particles by binding thereof, vertical axis represents fluorescence intensity and horizontal axis represents FITC labeled anti-sheep antibody IgG solution concentration. Lower graph is a chart which shows that each peak varies in concentration dependent fashion by antibody concentration. (Graph at upper part in FIG. 17 shows plotting of the results shown in the following table and findings by the flow cytometry are shown at lower part.)

| Ab(ng/ml) | GeoMean |
|---|---|
| 0.01 | 1.81 |
| 0.03 | 4.16 |
| 0.1 | 11.71 |
| 0.3 | 51.59 |
| 1 | 178.94 |
| 3 | 530.67 |
| 10 | 1245.35 |
| 30 | 2033.65 |
| 100 | 2911.65 |

Experiment 3

After sheep anti-glutathione S-transferase antibody solution at various concentrations (20-10,000 ng/ml) was mixed to 5 μl of the particle solution, 5 μl of 5 mg/ml bovine serum albumin aqueous solution was added and blocking was performed. Next, 5 μl of 25 μg/ml FITC labeled anti-sheep antibody IgG solution was added, mixed well, diluted with 480 μl of distilled water (without allowing time especially for reaction), and measured by the flow cytometry.

Figure 18:
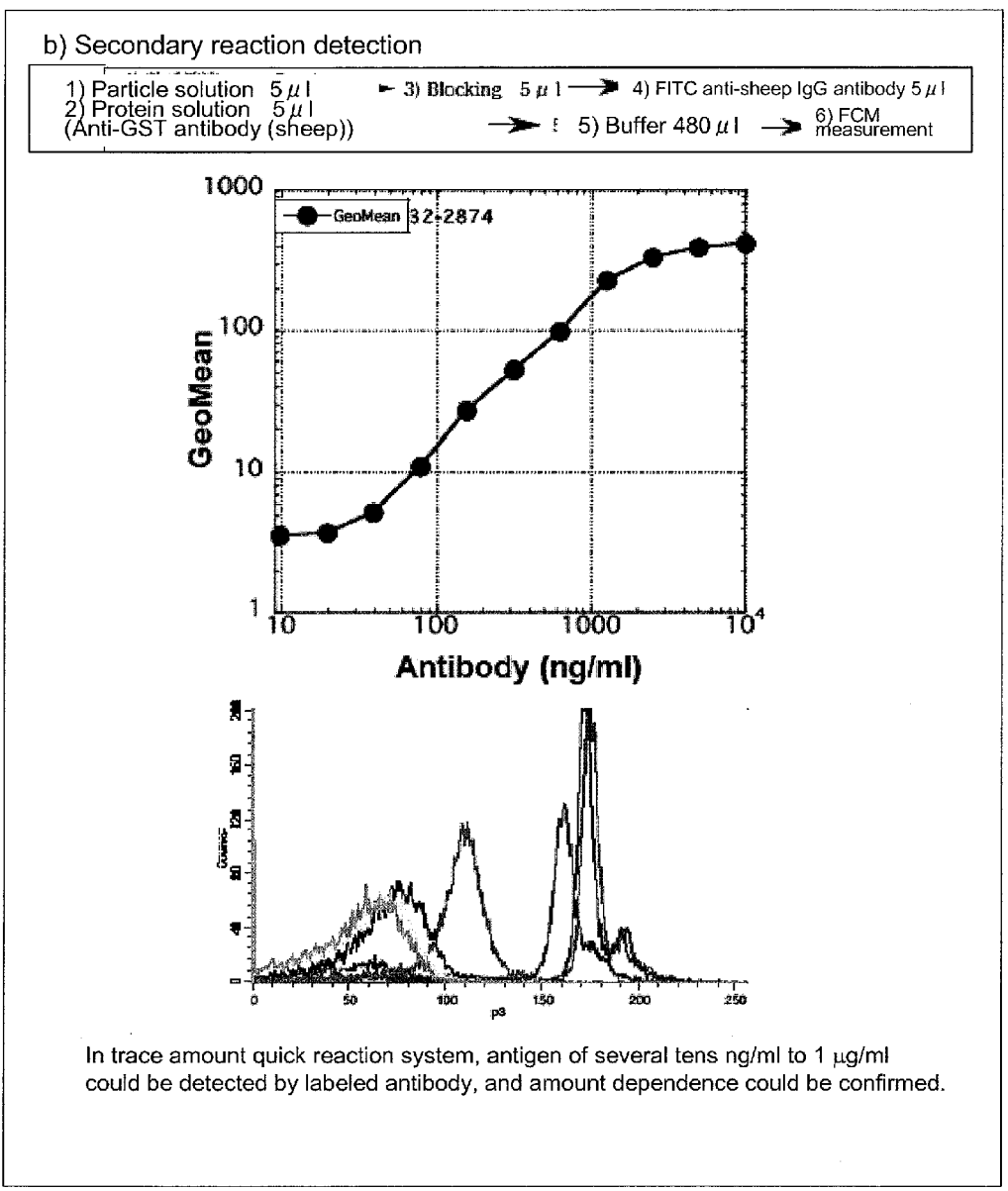
FIG. 18 shows that FITC labeled anti-sheep antibody IgG solution binds in short time to particles of sheep anti-glutathione-S-transferase antibody solution, being antigen, in concentration dependent fashion, upper graph shows correlation between concentration of sheep anti-glutathione-S-transferase antibody solution and fluorescence intensity detected from particles by binding thereof, vertical axis represents fluorescence intensity and horizontal axis represents concentration of sheep anti-glutathione-S-transferase antibody solution. Further, lower graph is a chart and shows that each peak varies in concentration dependent fashion by antibody concentration. These experimental results show that multiple-stage binding reaction occurs in amount dependent fashion on the particles, thereby resulting in the detection.

FIG. 18 shows that FITC labeled anti-sheep antibody IgG solution binds in short time to particles of sheep anti-glutathione-S-transferase antibody solution, being antigen, in concentration dependent fashion, upper graph shows correlation between concentration of sheep anti-glutathione-S-transferase antibody solution and fluorescence intensity detected from particles by binding thereof, vertical axis represents fluorescence intensity and horizontal axis represents sheep anti-glutathione-S-transferase antibody solution concentration. Further, lower graph is a chart and shows that each peak varies in antibody concentration dependent fashion. Experimental results show that multiple-stage binding reaction occurs in amount dependent fashion on the particles, thereby resulting in the detection. (Graph at upper part in FIG. 18 shows plotting of the results shown in the following table and findings by the flow cytometry are shown at lower part.)

| Ab(ng/ml) | GeoMean |
|---|---|
| 9.766 | 3.53 |
| 19.53125 | 3.75 |
| 39.0625 | 5.21 |
| 78.125 | 10.95 |
| 156.25 | 26.55 |
| 312.5 | 52.22 |
| 625 | 97.39 |
| 1250 | 230.32 |
| 2500 | 332.37 |
| 5000 | 393.91 |
| 10000 | 419.14 |

Accordingly, it can be interpreted that quantitative determination is possible using particles obtained by the present invention, and since with "non-pored particle" of the present invention, effective adherence area is simply depending upon particle diameter of particles, it has been revealed to be advantageous in quantitative experiments. Labeled antibodies several tens ng-1 μg/ml could be detected by trace amount quick reaction system, thereby confirming amount dependence.

Quantitative determination by flow cytometry has not been generalized yet even for particles with pore. One reason for that is difficulty of controls of effective adherence surface area. In addition, for conventional method, no report is available till today which reports good repeatability of signals suited for quantitative determination relating to scattered light (FSC, SCC) required for quantitative determination in the flow cytometry. Therefore, identification of a group of particles with fluorescence variation is difficult as long as conventional art is involved, and hence, it is considered that drawbacks of difficulty of accurate quantitative determination are not removed. According to general method, a group of particles is first identified by scattered light in the flow cytometry and then changes in the fluorescence of the group of particles are measured. Therefore, it is apparent that, contrary to those by the present invention, favorable application of the conventional technology with insufficient scattered light assessment to beads assay is not practical. (For example, although results of the flow cytometry by the conventional method are shown in Patent Document 2, signals of particles are distributed over extremely broader range, and no correlation is recognized between each of parameters.) In light of this point, it is shown that silica particle of the present invention can be utilized for bar-coding using differences of particle size and fluorescence for high-throughput analysis.

Comparative Example 4

Comparison Between Particles of the Present Invention and Commercial Standard Beads Size distribution of particles was assessed using flow cytometry. Comparison was performed also with commercial standard beads—Fluoresbrite from Polyscience Corp. Side scatter (SSC) was used for parameters for flow cytometry. Procedures, conditions and protocol for comparative experiments are as shown below. Thiol silica particles of the present invention (MPS, MPES, MPDMS) were synthesized as described in Example 2 or Example 5. Dilution of particles was performed, and measurement and assessment were performed by flow cytometry FACS Calibur HG.

Figure 21:
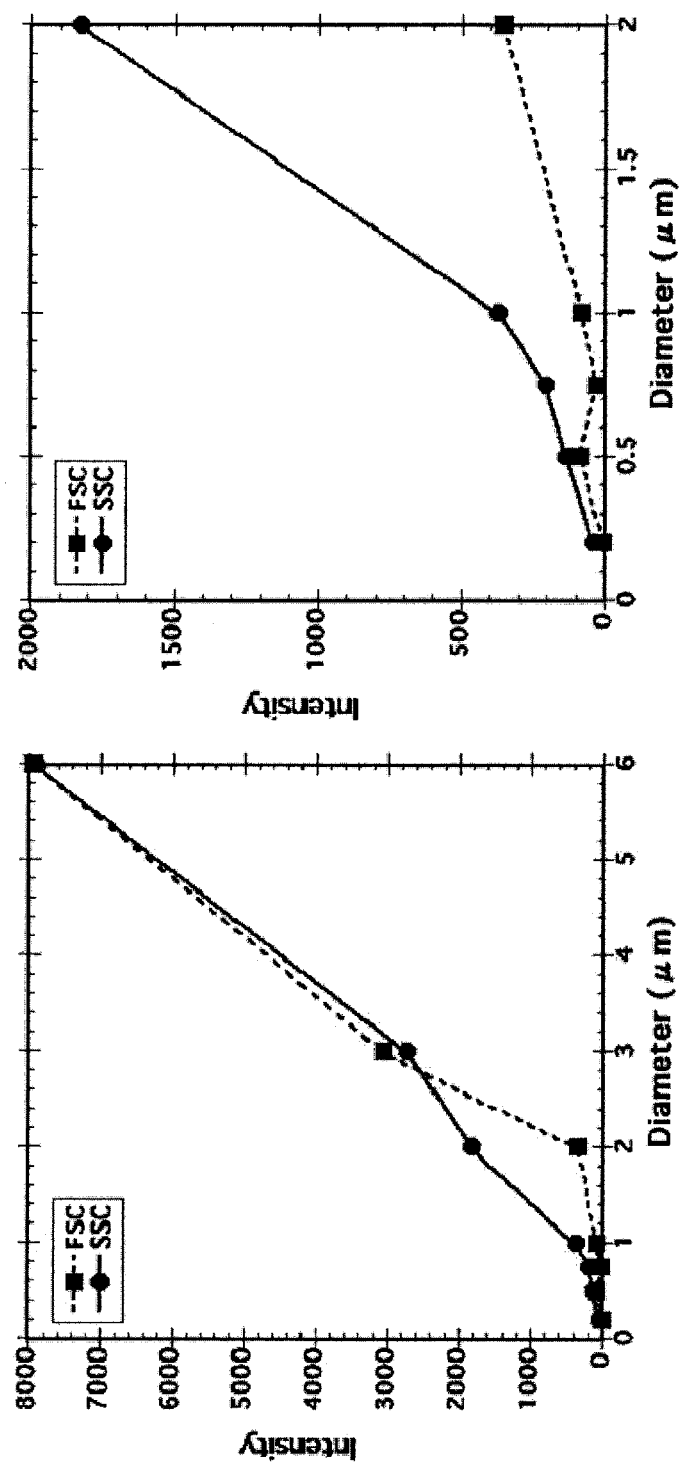
In FIG. 21, diameter of beads from 0.25 μm to 6 μm as well as values of FSC and SSC are plotted. It is noticed from left graph that both FSC and SSC well correlate with size at 3 μm or more and from right graph that SSC correlates more with size than FSC at 2 μm or less.

The reason why side scatter was employed instead of forward scatter is attributable to the data shown in FIG. 21. That is, if beads diameter from 0.25 μm to 6 μm, and FSC and SSC values are plotted (FIG. 21 left), there is a correlation between intensity and size for both FSC and SSC for not less than 3 μm, while for not more than 2 μm, SSC shows good correlation rather than FSC (FIG. 21 right), resulting in employing side scatter.

Figure 19:
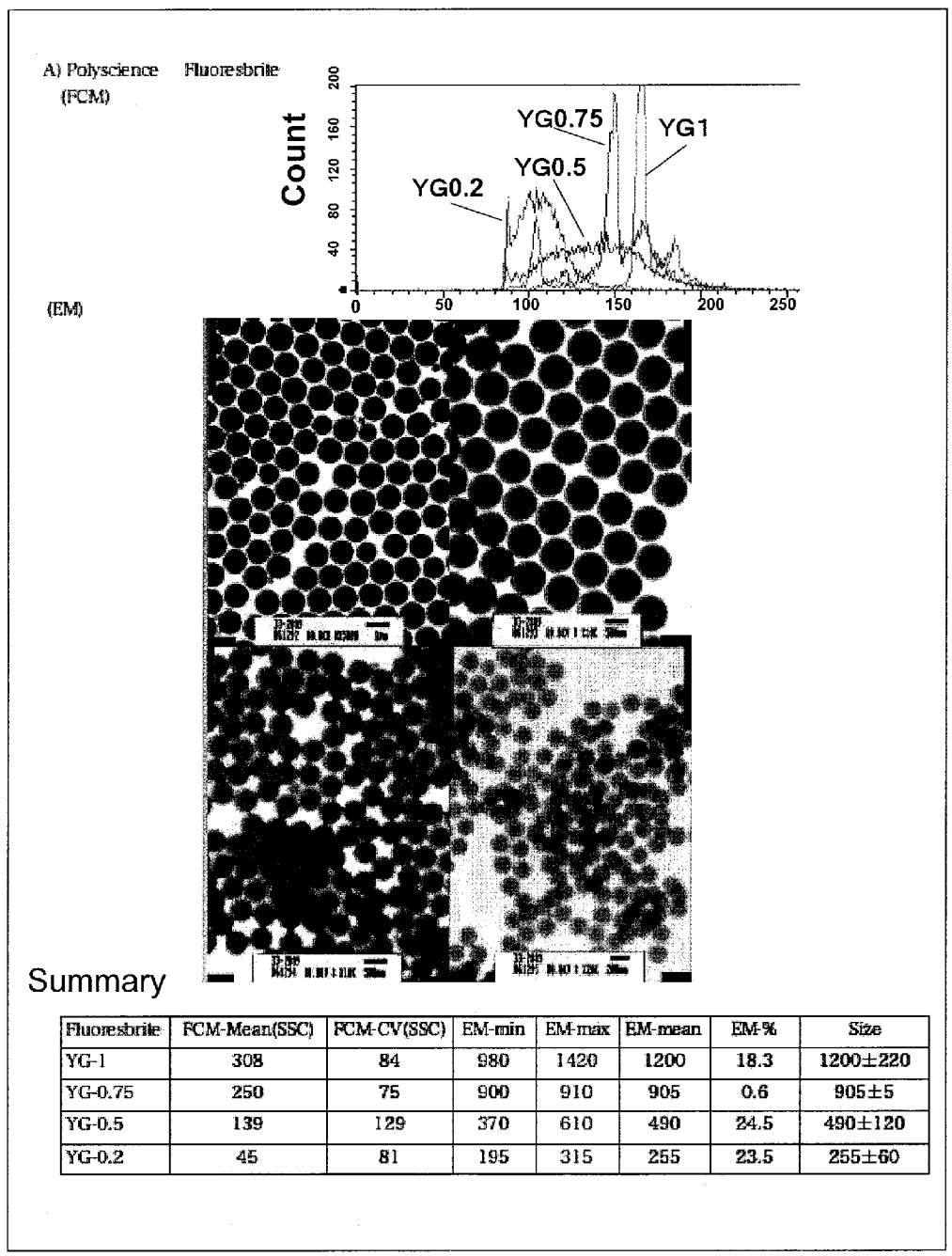
In FIG. 19, measurement results by flow cytometry (average value FCM-GeoMean, variation coefficient FCM-CV) for Fluoresbrite by Polyscience Corp. are shown in the table at the bottom, and findings by the electron microscope are summarized (minimum particle diameter EM-min and maximum EM-max, average EM-mean, size yield EM-%, size width size). Results of flow cytometry are shown at the top. The results show that SSC of particles are detected respectively and distribution of signals can be confirmed as a peak.
Figure 20:
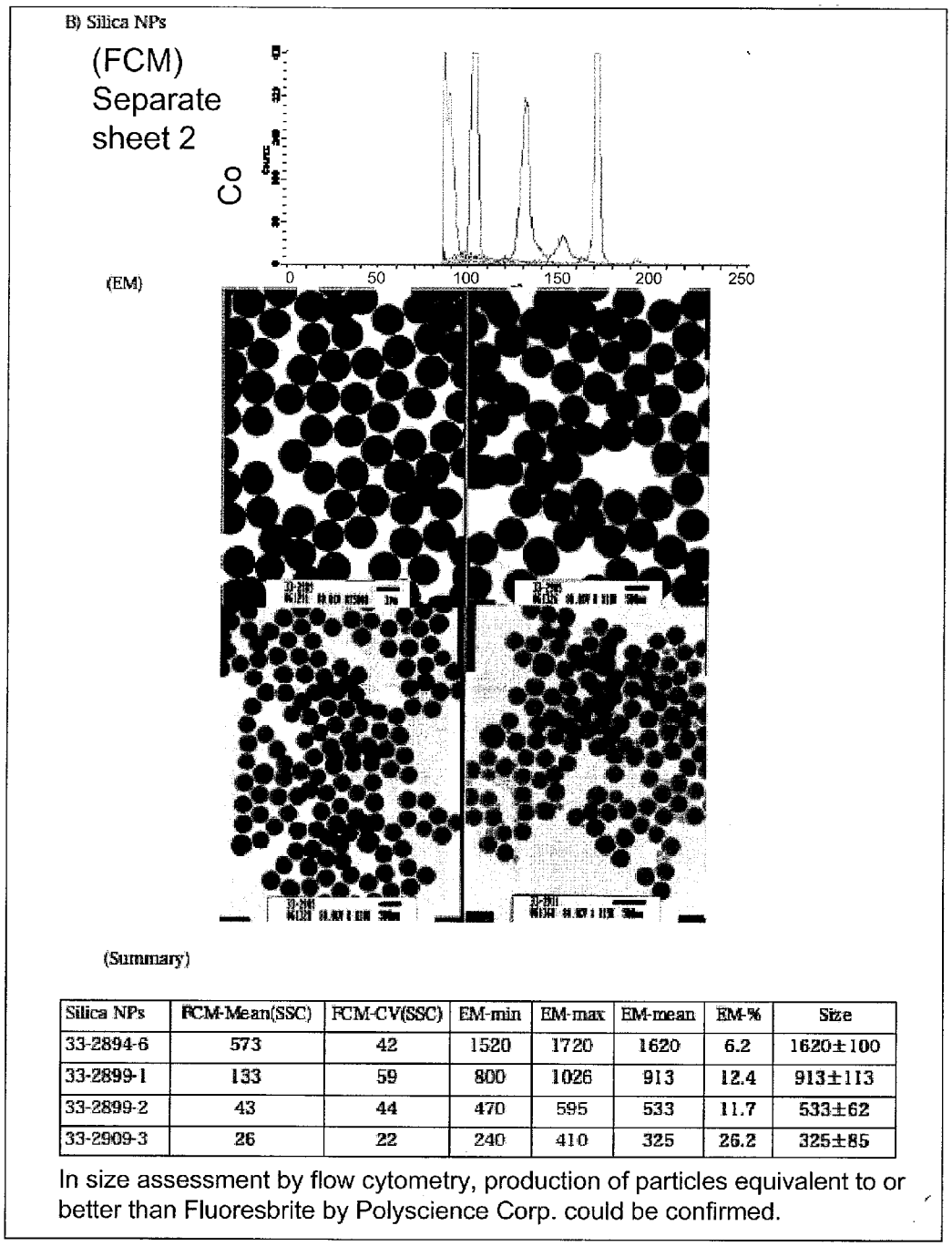
In FIG. 20, upper left: 33-2894-6, upper right: 33-2899-1, lower left: 33-2899-2, lower right: 33-2909-3.). It is known from these microscopic images that each particle is well controlled in size.

In the table shown at the lowest in FIG. 19 (Fluoresbrite from Polyscience Corp.) and FIG. 20 (particles by the present invention), measurement results by the flow cytometry (average value FCM-GeoMean, variation coefficient FCM-CV), and findings by the microscope (particle diameter minimum EM-min and maximum EM-max, average value EM-mean, size yield EM-%, size width size) are summarized.

Upper area shows results of the flow cytometry. These results indicate that SSC of particles is detected respectively and distribution of signals can be confirmed as a peak. (FIG. 19; green; YG1, pink: YG-0.75, light blue; YG-0.5, orange; YG-0.2, FIG. 20; green; 33-2894-6, pink: 33-2899-1, light blue; 33-2899-2, orange; 33-2909-3)

Further, middle area shows electron microscopic images of each particle. (FIG. 19; upper left; YG1, upper right: YG-0.75, lower left; YG-0.5, lower right; YG-0.2, FIG. 20; upper left; 33-2894-6, upper right; 33-2899-1, lower left; 33-2899-2, lower right; 33-2909-3) It is understood from these microscopic images that size of each particle is controlled favorably. Silica particles used here were synthesized according to descriptions of Examples 2-5, 13-17.

(Discussion for Comparison Between Beads Assay and Commercial Standard Beads)

Although results shown in (Embodiment of application to beads assay) and (Comparison with commercial standard beads) include some deviations between assessment by flow cytometry and assessment by electron microscope, favorable size control was confirmed with both commercial standard beads and beads of the present invention. Finding from assessment by flow cytometry showed that beads of the present invention are virtually favorable as compared with commercial standard beads.

Example 27

Measurement of Pore Volume or the Like by BET

Using BET method, pore distribution and specific surface area of nano silica particles of the present invention (MPES) were measured. As measuring instrument, specific surface area pore distribution measuring device SA-3100 from Beckman-Coulter Corp. was used. Pore volume was 0.0159 ($m^3$/g). Pore volume is small as the number of pores is low. Pore volume of nano silica particles of the present invention is at least less than 0.1 ($m^3$/g) even though various possibilities are taken into considerations. As for pore volume, influences of particle size are little, and characterization to be particles with small number of pores may be possible.

Example 28

Preparation of Silica Particles by MPS and EpoS 4.75 μl of MPS, 6.25 μl of EpoS, and 455 μl of 28% by weight ammonia water were added and mixed, and reacted at a high temperature (99° C. by heat block). Next, the reaction completed solution was observed by the electron microscope. As a result, formation of nano silica particles was confirmed.

Example 29

Preparation of Silica Particles by MPS and MPDMS 0.59 μl of MPS, 0.59 μl of MPDMS, and 462 μl of 28% by weight ammonia water were added and mixed, and reacted at 25 degrees Celsius for 24 hours. Next, the reaction completed solution was observed by the electron microscope. As a result, formation of nano silica particles was confirmed.

Example 30

Preparation of Silica Particles by MPES and MPDMS 0.59 μl of MPES, 0.94 μl of MPDMS, and 451 μl of 28% by weight ammonia water were added and mixed, and reacted at 25 degrees Celsius for 24 hours. Next, the reaction completed solution was observed by the electron microscope. As a result, formation of nano silica particles was confirmed.

Example 31

Cell Labeling and Detection by Nano Silica Particle Probe Containing Rhodamine

Silica particles to be used were synthesized according to the description of Example 6. Nano silica particles containing rhodamine were given intraperitoneally to mouse (Balbc/6J, 9-weeks old, male). Cells in the peritoneal cavity were collected next day. Observation of cells obtained by the fluorescence microscope revealed cells with which fluorescence of rhodamine was admitted as shown in the figure. Additional observation of intraperitoneal cells by the electron microscope revealed nano silica particles in cell cytoplasm as shown in the figure. These observations indicate that cells could be labeled using fluorescence nano silica particle as the probe by use of phagocytic capacity of macrophage. Further, labeled cells can be detected as fluorescence by fluorescence microscope and as particle images by electron microscope.

INDUSTRIAL APPLICABILITY

The present invention can be provided and utilized as a labeling substance or a marker for qualitative test and quantitative test for such as prophylactic agent, therapeutic agent, diagnostic agent, diagnostic and therapeutic agent or the like in dental, medical and veterinary fields regardless of fields.

In light of physical and chemical properties of nano particles of the present invention described above, nano particles of the present invention can be utilized in application fields of industrial materials as well as pharmaceutical and cosmetic materials such as nano structure reforming material, optical function coating material, fluorescent material, electronic parts material, magnetic recording material, and polishing material.

What is claimed is:

1. A silica particle prepared by a method consisting of:
   (a) mixing one or more silica compound and ammonia water, the silica compound being selected from a group consisting of mercapto-propyl-trimethoxysilane (MPS), mercapto-propyl-triethoxysilane (MPES), mercapto-propyl-methyldimethoxysilane (MPDMS), trimethoxy[2-(7-oxabicyclo[4.1.0]-hepto-3-yl)ethyl]silane (EpoPS), thiocyanatopropyltriethoxysilane (TCPS), and acryloxypropyltrimethoxysilane (AcPS) and
   (b) reacting the silica compound and the ammonia water under a predetermined temperature condition, wherein the ammonia water and temperature condition in steps (a) and (b) satisfy either or both of the following conditions:
      (i) high temperature in a range of 80-100° C.; and
      (ii) high ammonia concentration at a final concentration not less than 25%.

2. The silica particle according to claim 1, further coupled to a support used for synthesis of nucleic acid or protein, or cell culture application.

3. The silica particle according to claim 1 wherein the method is performed so that ammonia water and temperature condition in steps (a) and (b) satisfy both of the conditions (i) and (ii).

4. The silica particle according to claim 1 wherein the condition (i) is in a range of 90-100° C.; and the final concentration of ammonia water per condition (ii) is not less than 27% by weight.

5. The silica particle according to claim 1, wherein said step (b) is performed in the presence of isopropanol.

6. The silica particles according to claim 1, having one or more feature selected from a group consisting of:
   (1) being non-pored;
   (2) being free from macropore;
   (3) being substantially in spherical shape;
   (4) being free from pore not less than 20 nm;
   (5) pore volume being not more than 0.1 ($m^3$/kg); and
   (6) particle diameter being in a range of 5 nm to 5 μm.

7. A standard marker including the silica particle according to claim 1, used for flow cytometry, size marker, beads assay and probe, the silica particle further containing a functional material on surface layer or therein, wherein the functional material is selected from a group consisting of fluorescent material, protein, nucleotide, oligonucleotide, sugar chain and combinations thereof.

8. A group of silica particles, produced by a method consisting of:
   (a) mixing one or more silica compound and ammonia water, the one or more silica compounds being selected from a group consisting of mercapto-propyl-trimethoxysilane (MPS), mercapto-propyl-triethoxysilane (MPES), mercapto-propyl-methyldimethoxysilane (MPDMS), trimethoxy[2-(7-oxabicyclo[4.1.0]-hepto-3-yl)ethyl]silane (EpoPS), thiocyanatopropyltriethoxysilane (TCPS), and acryloxypropyltrimethoxysilane (ALPS); and
   (b) reacting the silica compound and the ammonia water under a predetermined temperature condition, wherein the ammonia water and temperature condition in steps (a) and (b) satisfy either or both of the following conditions:
      (i) high temperature in a range of 80-100° C.; and
      (ii) high ammonia concentration at a final concentration not less than 25%,
   wherein the particles have,
      (1) average particle diameter adjusted in a range of 5 nm to 5 μm that is a range of nano size to micron size; and
      (2) narrow area distribution with distribution width of particle diameter within ±25% of average particle diameter,
   wherein the particles are dispersed.

9. The group of silica particles according to claim 8, further coupled to a support for synthesis of nucleic acid or protein, or cell culture application.

10. The group of silica particles according to claim 8 wherein the method is performed so that ammonia water and temperature condition in steps (a) and (b) satisfy both of the conditions (i) and (ii).

11. The group of silica particles according to claim 8 wherein the condition (i) is in a range of 90-100° C.; and the final concentration of ammonia water per condition (ii) is not less than 27% by weight.

12. The group of silica particles according to claim 8, wherein said step (b) is performed in the presence of isopropanol.

13. The group of silica particles according to claim 8, having one or more feature selected from a group consisting of:
   (1) being non-pored;
   (2) being free from macropore;
   (3) being substantially in spherical shape;
   (4) being free from pore not less than 20 nm;
   (5) pore volume being not more than 0.1 ($m^3$/kg); and
   (6) particle diameter being in a range of 5 nm to 5 μm.

14. A standard marker including the group of silica particles according to claim 8, used for flow cytometry, size marker, beads assay and probe, the silica particle further containing a functional material on surface layer or therein, wherein the functional material is selected from a group consisting of fluorescent material, protein, nucleotide, oligonucleotide, sugar chain and combinations thereof.

15. A preparation method of a silica particle or a group of silica particles consisting of;
   (a) preparing a mixture of silica compound and ammonia water; and
   (b) reacting the silica compound and the ammonia water under a predetermined temperature condition, wherein the silica compound is one or more silica compound selected from a group consisting of mercapto-propyl-trimethoxysilane (MPS), mercapto-propyl-triethoxysilane (MPES), mercapto-propyl-methyldimethoxysilane (MPDMS), trimethoxy[2-(7-oxabicyclo[4.1.0]-hepto-3-yl)ethyl]silane (EpoPS), thiocyanatopropyltriethoxysilane (TCPS), and acryloxypropyltrimethoxysilane (AcPS), and wherein,
   the method are performed so that ammonia water and temperature condition in steps (a) and (b) satisfy either of or both of the following conditions:
      (i) high temperature in a range of 80-100° C.; and
      (ii) high ammonia concentration at a final concentration not less than 25%.

16. The method according to claim 15, wherein said step (b) is performed in the presence of isopropanol.

17. The method according to claim 15 wherein the method is performed so that ammonia water and temperature condition in steps (a) and (b) satisfy both of the conditions (i) and (ii).

18. The method according to claim 15 wherein the condition (i) is in a range of 90-100° C.; and the final concentration of ammonia water per condition (ii) is not less than 27% by weight.

19. A silica particle containing a functional material therein, the silica particle being prepared by a method consisting of:
(a) mixing one or more silica compound, a functional material and ammonia water, the silica compound being consisting of one or more silica compound selected from a group consisting of mercapto-propyl-trimethoxysilane (MPS), mercapto-propyl-triethoxysilane (MPES), mercapto-propyl-methyldimethoxysilane (MPDMS), trimethoxy[2-(7-oxabicyclo[4.1.0]-hepto-3-yl)ethyl]silane (EpoPS), thiocyanatopropyltriethoxysilane (TCPS), and acryloxypropyltrimethoxysilane (AcPS) wherein the silica particle is prepared by:
(b) reacting the silica compound and the ammonia water, and wherein the ammonia water and temperature condition in steps (a) and (b) satisfy either of or both of the following conditions:
(i) high temperature (in a range of 80-100° C.) and
(ii) final concentration of ammonia water not less than 25% by weight,
wherein the functional material is selected from a group consisting of fluorescent material, protein, nucleotide, oligonucleotide, sugar chain and combinations thereof.

20. The silica particle according to claim 19, wherein when the functional material is a fluorescent material, the fluorescent material is selected from a group consisting of rhodamine red, fluorescein, hexanoic acid-6-(tetramethylrhodamine-5-carboxamide), hexanoic acid-5-(tetramethylrhodamine-5-carboxamide), and trisdichlororuthenium (II) hexahydrate, and the fluorescent material is contained inside.

21. The silica particle according to claim 19, wherein the functional material therein is fluorescent material.

22. The silica particle according to claim 19, wherein said functional material therein is a fluorescent material, wherein the fluorescent material is not in the form of being bound to a compound selected from N-hydroxy succinimide (NHS), isothiocyanate (ITC) and maleimide.

23. The silica particle according to claim 19, wherein a functional group is present in an unreacted form on the surface layer, wherein said functional group is selected from mercapto-propyl group, oxabicyclo[4.1.0]-hepto-3-yl)ethyl groups, thiocyanatopropyl group, and acryloxypropyl group.

24. A preparation method of a silica particle or a group of silica particles containing a functional material therein, the method comprising,
(a) preparing a mixture of one or more silica compounds, a functional material and ammonia water; and
(b) reacting the silica compound and the ammonia water under a predetermined temperature condition,
wherein, the silica compound is selected from a group consisting of mercapto-propyl-trimethoxysilane (MPS), mercapto-propyl-triethoxysilane (MPES), mercapto-propyl-methyldimethoxysilane (MPDMS), trimethoxy[2-(7-oxabicyclo[4.1.0]-hepto-3-yl)ethyl]silane (EpoPS), thiocyanatopropyltriethoxysilane (TCPS), and acryloxypropyltrimethoxysilane (AcPS), and wherein,
the method is performed so that ammonia water and temperature condition in steps (a) and (b) satisfy either of or both of the following conditions:
(i) high temperature (in a range of 80-100° C.); and
(ii) high ammonia concentration at a final concentration not less than 25%, wherein the functional material is selected from a group consisting of fluorescent material, protein, nucleotide, oligonucleotide, sugar chain and combinations thereof.

25. The method according to claim 24 wherein the method is performed so that ammonia water and temperature condition in steps (a) and (b) satisfy both of the conditions (i) and (ii).

26. The method according to claim 24 wherein the condition (i) is in a range of 90-100° C.; and the final concentration of ammonia water per condition (ii) is not less than 27% by weight.

* * * * *

UNITED STATES PATENT AND TRADEMARK OFFICE
CERTIFICATE OF CORRECTION

| | | |
|---|---|---|
| PATENT NO. | : 8,455,255 B2 | Page 1 of 1 |
| APPLICATION NO. | : 12/303870 | |
| DATED | : June 4, 2013 | |
| INVENTOR(S) | : Michihiro Nakamura | |

It is certified that error appears in the above-identified patent and that said Letters Patent is hereby corrected as shown below:

In the Claims

Column 39, Line 58:
"(ALPS); and" should read, --(AcPS); and--.

Signed and Sealed this
Fourteenth Day of January, 2014

Michelle K. Lee
*Deputy Director of the United States Patent and Trademark Office*